United States Patent
Murray

(10) Patent No.: US 11,076,846 B2
(45) Date of Patent: Aug. 3, 2021

(54) METHODS AND PROCEDURES FOR LIGAMENT REPAIR

(71) Applicant: The Children's Medical Center Corporation, Boston, MA (US)

(72) Inventor: Martha M. Murray, Sherborn, MA (US)

(73) Assignee: The Children's Medical Center Corporation, Boston, MA (US)

(*) Notice: Subject to any disclaimer, the term of this patent is extended or adjusted under 35 U.S.C. 154(b) by 30 days.

(21) Appl. No.: 16/558,824

(22) Filed: Sep. 3, 2019

(65) Prior Publication Data

US 2019/0388083 A1 Dec. 26, 2019

Related U.S. Application Data

(60) Division of application No. 16/228,196, filed on Dec. 20, 2018, now Pat. No. 10,786,238, which is a
(Continued)

(51) Int. Cl.
*A61B 17/04* (2006.01)
*A61B 17/11* (2006.01)
(Continued)

(52) U.S. Cl.
CPC ...... *A61B 17/0401* (2013.01); *A61B 17/1146* (2013.01); *A61F 2/0811* (2013.01); *A61L 17/12* (2013.01); *A61L 27/22* (2013.01); *A61L 27/24* (2013.01); *A61L 27/52* (2013.01); *A61L 27/56* (2013.01); *A61B 17/0469* (2013.01); *A61B 2017/00004* (2013.01); *A61B 2017/00893* (2013.01); *A61B 2017/044* (2013.01);
(Continued)

(58) Field of Classification Search
USPC ......... 623/13.11, 13.12, 13.14, 13.17, 13.18, 623/14.12, 23.72, 23.75, 23.76; 424/422, 424/426; 606/232, 286
See application file for complete search history.

(56) References Cited

U.S. PATENT DOCUMENTS 2,127,903 A  5/1936  Bowen
3,176,316 A  4/1965  Bodell
(Continued)

FOREIGN PATENT DOCUMENTS

CN  102488713 A  6/2012
EP  0295721 A2  12/1988
(Continued)

OTHER PUBLICATIONS

Masur et al., Myofibroblasts differentiate from fibroblasts when plated at low density, Proc. Natl. Acad. Sci. USA, Apr. 1996, pp. 4219-4223, Cell Biology, vol. 93.
(Continued)

*Primary Examiner* — Yashita Sharma
(74) *Attorney, Agent, or Firm* — Offit Kurman, P.A.; Gregory A. Grissett

(57) ABSTRACT

Methods and devices for the repair of a ruptured ligament using a scaffold device are provided. Aspects of the invention, may include a scaffold attached by a suture to an anchor. In aspects of the invention, the anchor may be secured to a bone near or at the repair site.

6 Claims, 8 Drawing Sheets

Related U.S. Application Data continuation of application No. 13/461,269, filed on May 1, 2012, now Pat. No. 10,786,232, which is a continuation of application No. 12/162,108, filed as application No. PCT/US2007/001908 on Jan. 25, 2007, now abandoned.

(60) Provisional application No. 60/761,951, filed on Jan. 25, 2006.

(51) Int. Cl.
*A61F 2/08* (2006.01)
*A61L 17/12* (2006.01)
*A61L 27/22* (2006.01)
*A61L 27/24* (2006.01)
*A61L 27/52* (2006.01)
*A61L 27/56* (2006.01)
*A61B 17/00* (2006.01)

(52) U.S. Cl.
CPC .......... *A61B 2017/0414* (2013.01); *A61B 2017/0458* (2013.01); *A61F 2002/0888* (2013.01); *A61L 2430/10* (2013.01)

(56) References Cited

U.S. PATENT DOCUMENTS

| | | | |
|---|---|---|---|
| 3,195,778 A | 7/1965 | Coates | |
| 3,373,906 A | 3/1968 | DeHart et al. | |
| 3,587,982 A | 6/1971 | Campbell | |
| 3,738,535 A | 6/1973 | Nicholls | |
| 3,774,604 A | 11/1973 | Danielsson | |
| 3,797,499 A | 3/1974 | Schneider | |
| 3,893,834 A | 7/1975 | Armstrong | |
| 4,069,814 A | 1/1978 | Clemens | |
| 4,186,448 A | 2/1980 | Brekke | |
| 4,265,618 A | 5/1981 | Herskovitz et al. | |
| 4,326,540 A | 4/1982 | Bailey et al. | |
| 4,458,678 A | 7/1984 | Yannas et al. | |
| 4,467,806 A | 8/1984 | Bhiwandiwala et al. | |
| 4,578,067 A | 3/1986 | Cruz, Jr. | |
| 4,585,458 A | 4/1986 | Kurland | |
| 4,753,536 A | 6/1988 | Spehar et al. | |
| 4,808,184 A | 2/1989 | Tepic | |
| 4,808,570 A | 2/1989 | Michaeli | |
| 4,846,835 A | 7/1989 | Grande | |
| 4,851,513 A | 7/1989 | Devore et al. | |
| 4,894,063 A | 1/1990 | Nashef | |
| 4,932,942 A | 6/1990 | Maslanka | |
| 4,955,893 A | 9/1990 | Yannas et al. | |
| 4,959,058 A | 9/1990 | Michelson | |
| 4,973,321 A | 11/1990 | Michelson | |
| 5,007,934 A | 4/1991 | Stone | |
| 5,037,396 A | 8/1991 | Streeter | |
| 5,078,744 A | 1/1992 | Chvpil | |
| 5,119,669 A | 6/1992 | Silvis et al. | |
| 5,152,462 A | 10/1992 | Evans | |
| 5,171,273 A | 12/1992 | Silver et al. | |
| 5,206,023 A | 4/1993 | Hunziker | |
| 5,206,028 A | 4/1993 | Li | |
| 5,275,826 A | 1/1994 | Badylak et al. | |
| 5,281,422 A | 1/1994 | Badylak et al. | |
| 5,380,087 A | 1/1995 | Haber et al. | |
| 5,436,135 A | 7/1995 | Tayot et al. | |
| 5,455,833 A | 10/1995 | Herre et al. | |
| 5,474,450 A | 12/1995 | Chronister | |
| 5,503,616 A | 4/1996 | Jones | |
| 5,522,840 A | 6/1996 | Krajicek | |
| 5,556,429 A | 9/1996 | Felt | |
| 5,595,621 A | 1/1997 | Light et al. | |
| 5,652,077 A | 7/1997 | Obinata | |
| 5,655,546 A | 8/1997 | Halpern | |
| 5,681,353 A | 10/1997 | Li et al. | |
| 5,713,374 A | 2/1998 | Pachence et al. | |
| 5,749,895 A | 5/1998 | Sawyer et al. | |
| 5,810,884 A | 9/1998 | Kim | |
| 5,897,591 A | 4/1999 | Kobayashi | |
| 5,902,741 A | 5/1999 | Purchio et al. | |
| 5,968,018 A | 10/1999 | Freeman et al. | |
| RE36,370 E | 11/1999 | Li | |
| 6,045,549 A | 4/2000 | Smethers et al. | |
| 6,080,192 A | 6/2000 | Demopulos et al. | |
| 6,087,113 A | 7/2000 | Caplan et al. | |
| 6,096,309 A | 8/2000 | Prior et al. | |
| 6,117,425 A | 9/2000 | MacPhee et al. | |
| 6,129,757 A | 10/2000 | Weadock | |
| 6,139,520 A | 10/2000 | McCrory et al. | |
| 6,153,292 A | 11/2000 | Bell et al. | |
| 6,171,610 B1 | 1/2001 | Vacanti et al. | |
| 6,176,880 B1 | 1/2001 | Plouhar et al. | |
| 6,214,049 B1 | 4/2001 | Garyer et al. | |
| 6,234,795 B1 | 5/2001 | Fischer | |
| 6,280,474 B1 | 8/2001 | Cassidy et al. | |
| 6,283,996 B1 * | 9/2001 | Chervitz ............ A61B 17/0401 623/13.14 |
| 6,309,372 B1 | 10/2001 | Fischer et al. | |
| 6,365,149 B2 | 4/2002 | Vyakarnam et al. | |
| 6,398,761 B1 | 6/2002 | Bills et al. | |
| 6,454,129 B1 | 9/2002 | Green | |
| 6,472,210 B1 | 10/2002 | Holy et al. | |
| 6,629,997 B2 | 10/2003 | Mansmann | |
| 6,689,153 B1 | 2/2004 | Skiba | |
| 6,699,214 B2 | 3/2004 | Gellman | |
| 6,946,003 B1 | 9/2005 | Wolowacz et al. | |
| 6,964,685 B2 | 11/2005 | Murray et al. | |
| 6,971,787 B2 | 12/2005 | Botrie et al. | |
| 6,989,034 B2 | 1/2006 | Hammer et al. | |
| 7,119,062 B1 | 10/2006 | Alvis et al. | |
| 7,148,209 B2 | 12/2006 | Hoemann et al. | |
| 7,156,880 B2 | 1/2007 | Evans et al. | |
| 7,250,057 B2 | 7/2007 | Forsberg | |
| 7,335,220 B2 | 2/2008 | Khosravi et al. | |
| 7,652,077 B2 | 1/2010 | Cook et al. | |
| 7,838,630 B2 | 11/2010 | Murray et al. | |
| 7,901,461 B2 | 3/2011 | Harmon et al. | |
| 8,002,813 B2 | 8/2011 | Scarborough et al. | |
| 8,137,686 B2 | 3/2012 | Kladakis et al. | |
| 8,308,681 B2 | 11/2012 | Slocum et al. | |
| 8,642,735 B2 | 2/2014 | Murray et al. | |
| 9,308,242 B2 | 4/2016 | Murray | |
| 9,757,495 B2 | 9/2017 | Murray | |
| 9,849,213 B2 | 12/2017 | Murray | |
| 2002/0022884 A1 | 2/2002 | Mansmann | |
| 2002/0123805 A1 | 9/2002 | Murray et al. | |
| 2002/0161450 A1 | 10/2002 | Doi et al. | |
| 2002/0183845 A1 | 12/2002 | Mansmann et al. | |
| 2003/0012805 A1 | 1/2003 | Chen et al. | |
| 2003/0078659 A1 | 4/2003 | Yang | |
| 2003/0147935 A1 | 8/2003 | Binette et al. | |
| 2003/0163144 A1 | 8/2003 | Weadock et al. | |
| 2003/0167053 A1 | 9/2003 | Taufig | |
| 2003/0236573 A1 | 12/2003 | Evans et al. | |
| 2004/0059416 A1 * | 3/2004 | Murray ................ A61L 24/043 623/13.15 |
| 2004/0078077 A1 | 4/2004 | Binette et al. | |
| 2004/0170664 A1 | 9/2004 | Spector et al. | |
| 2004/0243235 A1 * | 12/2004 | Goh .......................... A61F 2/08 623/13.17 |
| 2004/0258729 A1 | 12/2004 | Czemuszka et al. | |
| 2004/0262332 A1 | 12/2004 | Pauser et al. | |
| 2004/0267362 A1 | 12/2004 | Hwang et al. | |
| 2005/0027307 A1 | 2/2005 | Schwartz et al. | |
| 2005/0129730 A1 | 6/2005 | Pang et al. | |
| 2005/0183731 A1 | 8/2005 | Hunter et al. | |
| 2005/0230422 A1 | 10/2005 | Muller et al. | |
| 2005/0261736 A1 | 11/2005 | Murray et al. | |
| 2005/0267521 A1 | 12/2005 | Forsberg | |
| 2007/0269476 A1 | 11/2007 | Voytik-Harbin et al. | |
| 2008/0195205 A1 | 8/2008 | Schwartz | |
| 2009/0143765 A1 | 6/2009 | Slocum et al. | |
| 2009/0254104 A1 | 10/2009 | Murray | |
| 2009/0306776 A1 | 12/2009 | Murray | |
| 2010/0221835 A1 | 9/2010 | Tanaka et al. | |

(56) References Cited

U.S. PATENT DOCUMENTS

| | | |
|---|---|---|
| 2011/0027338 A1 | 2/2011 | Murray et al. |
| 2011/0306555 A1 | 12/2011 | Murray et al. |
| 2012/0201896 A1 | 8/2012 | Murray et al. |
| 2012/0283831 A1 | 11/2012 | Murray |
| 2013/0231609 A1 | 9/2013 | Slocum et al. |
| 2013/0273017 A1 | 10/2013 | Murray |
| 2014/0134249 A1 | 5/2014 | Murray et al. |
| 2014/0369984 A1 | 12/2014 | Murray et al. |
| 2015/0367030 A1 | 12/2015 | Murray |
| 2016/0206779 A1 | 7/2016 | Murray |
| 2016/0263279 A1 | 9/2016 | Murray et al. |
| 2017/0340772 A1 | 11/2017 | Murray |
| 2018/0207316 A1 | 7/2018 | Murray |
| 2019/0134269 A1 | 5/2019 | Murray et al. |

FOREIGN PATENT DOCUMENTS

| | | |
|---|---|---|
| EP | 0445951 A2 | 9/1991 |
| EP | 0645149 A1 | 3/1995 |
| EP | 1254671 A1 | 11/2002 |
| EP | 1273312 A1 | 1/2003 |
| GB | 2106794 A | 4/1983 |
| WO | 8500511 A1 | 2/1985 |
| WO | 9213565 A1 | 8/1992 |
| WO | 9311723 A1 | 6/1993 |
| WO | 9321857 A1 | 11/1993 |
| WO | 9525550 A1 | 9/1995 |
| WO | 9940771 A1 | 8/1999 |
| WO | 2000047130 A1 | 8/2000 |
| WO | 2000074760 A2 | 12/2000 |
| WO | 2001066130 A1 | 9/2001 |
| WO | 2002067812 A2 | 9/2002 |
| WO | 2003105737 A1 | 12/2003 |
| WO | 2004078134 A2 | 9/2004 |
| WO | 2008036393 A1 | 3/2008 |
| WO | 2008060361 A2 | 5/2008 |
| WO | 2008109407 A2 | 9/2008 |
| WO | 2008109807 A2 | 9/2008 |
| WO | 2010048418 A1 | 4/2010 |
| WO | 2010084481 A1 | 7/2010 |
| WO | 2010108237 A1 | 9/2010 |
| WO | 2013116744 A1 | 8/2013 |

OTHER PUBLICATIONS

Murray et al., Migration of Human Anterior Cruciate Ligament Fibrosis Into Porous Collagen-GAG Matrices In Vitro, 24th Annual Meeting of the Society for Biomaterials, San Diego, CA, Apr. 22-26, 1996, pp. 463.

Murray et al., The Migration of Human Anterior Cruciate Ligament Fibroblasts Into Porous Collagen-GAG Matrices In Vitro, 45th Annual Meeting, Orthopaedic Research Society, Anaheim, CA, Feb. 1-4, 1999, 1 pp.

Murray et al., Differences in the Outgrowth of Cells from Explants from the Proximal and Distal Human ACL and Responses to TGF-B1, 47th Annual Meeting, Orthopaedic Research Society, San Francisco, CA, Feb. 25-28, 2001, pp. 0788.

Murray et al., The Effects of Selected Growth Factors on Human ACL Cell Interactions with 3-D Collagen-GAG Scaffolds, 47th Annual Meeting, Orthodaedic Research Society, San Francisco, CA, Feb. 25-28, 2001, pp. 0790.

Murray et al., The migration of cells from the ruptured human anterior cruciate ligament into collagen-glycosaminoglycan regeneration templates in vitro, Biomaterials 22, 2001 Elsevier, pp. 2393-2402.

Murray et al., The Effect Ruptured Human Anterior Cruciate Ligament Histology on Cell Interactions with a Collagen-GAG Scaffold In Vitro, Davos Tissue Engineering Workshop, Davos Switzerland, 2000, I pp.

Murray et al., Histological Changes in the Human Anterior Cruciate Ligament After Rupture, The Journal of Bone and Joint Surgery Incorporated, Oct. 2000, pp. 1387-1397, vol. 82-A, No. 10.

Murray et al., Fibroblast Distribution in the Anteromedial Bundle of the Human Anterior Cruciate Ligament: The Presence of alpha smooth muscle actin-positive cells, J. Orthop. Res., 1999, pp. 18-27, vol. 17., No. 1.

Murray et al., Migration os Cells from Human Anterior Cruciate Ligament Explants into Collagen-Glycosaminoglycan Scaffolds, Journal of Orthopaedic Research, 2000., pp. 557-564, vol. 18, No. 4.

Murray et al., Migration of Cells fro mRuptured Human Anterior Curciate Ligament Explants Into Collagen-GAG Matrices, 6th World Biomatrials Conference, Kamuela, HI, 2000, 1 pp.

Murray et al., Use of a Collagen-Platelet Rich Plasma Scaffold to Stimulate Healing of a Central Defect in the Canine ACL, Journal of Orthopaedic Research, Apr. 2006, pp. 820-830, Wilet InterScience.

Nakamura et al., A Comparison of in vivo gene delivery methods for antisense therapy in ligament healing, Gene Therapy, 1998, pp. 1455-1461, vol. 5.

Nakamura et al., Early biological effect of in vivo gene transfer of platelet-derived growth factor (PDGF)-B into healing patellar ligament, Gene Therapy, 1998, pp. 1165-1170, vol. 5.

Neuman et al. The Determination of Hydroxyproline, J. Biol. Chem, 184, 1950, pp. 299-306.

Niklason et al., Functional arteries grown in vitro, Copyright American Association for the Advancement of Science, Washington, Apr. 16, 1999, 6 pp.

[No Author Listed], Guidance Document for Testing Biodegradable Polymer Implant Devices, ODE Guidance Documents, Apr. 20, 1996, 11 pp.

[No Author Listed], Meriam Webster Dictionary, Definition carbonate-apatite, 7 pp.

Noyes et al., Bone-Patellar Ligament-Bone and Fascia Lata Allografts for Reconstruction of the Anterior Cruciate Ligament, The Journal of Bone and Joint Surgery, 1990, pp. 1125-1136, vol. 72-A, No. 8.

Officer Anita Meacle, European Office Action, European Patent Application No. 07 867 174.0, dated Nov. 29, 2018, 5 pp.

Peter et al., Synthesis of poly (propylene fumarate) by acylation of propylebe glycol in the presence of a proton scavenger, Journal of Biomaterial Science, Polymer Edition, 1999, pp. 363-373, vol. 10, No. 3.

Qui et al. Outgrowth of chondrocytes from human articular cartilage explants and ecpression of alpha-smooth muscle actin, Wound Repair an d Regeneration, Sep.-Oct. 2000, pp. 383-391, vol. 8, No. 5.

Sadowska et al., Isolation of collagen from the skins of Baltic cod (*Gadus morhua*), Food Chemistry, 2003, pp. 257-262, Elsevier Science, Ltd.

Schmidt et al., Effect of Growth Factors on the Proliferation of Fibroblasts from the Medical Collateral and Anterior Cruciate Ligaments, Journal of Orthopaedic Research, The Journal of Bone and Joint Surged, Inc., 1995, pp. 184-190, vol. 13, No. 2.

Schulz Torres et al., Effects of Modulus of Elasticity of Collagen Sponges on Their Cell-Mediacted Contraction In Vitro, Massachusetts Institute of Technology, Jun. 1998, 96 pp.

Spindler et al., Comparison of Collagen Synthesis in the Peripheral and Central Region of the Canine Meniscus, Clinical Orthopaedics, Jun. 1994, pp. 256-263, vol. 303.

Spindler et al., Regional Mitogenic Response of the Meniscus to Platelet-Derived Growth Factor (PDGF-AB), Journal of Orthopaedic Research, The Journal od Bone and Joint Surgery, Inc., 1995, pp. 201-207, vol. 13, No. 2.

Spindler et al., Patellar Tendon and Anterior Cruciate Ligament Have Different Mitogenic Responses to Platelet-Derived Growth Factor and Transforming Growth Factor Beta, Journal of Orthpaedic Research, The Journal of Bone and Joint Surgery, Inc., 1996, pp. 542-546, vol. 14, No. 4.

Stensel et al., Collagen as a Biomaterial, Annual Review Biophysics Bioenginering, 1974, 24 pp.

Stevenson et al., Gender Differences in Knee Injury Epidemiology Among Competitive Alpine Ski Racers, The Iowa Orthopaedic Journal, 1998, pp. 64-66, vol. 18.

(56) References Cited

OTHER PUBLICATIONS

Stone et al., Future Directions Collagen-Based Prosteses for Meniscal Regeneration, Clinical Orthopaedics and Related Research, Mar. 1990, pp. 129-136, No. 252.

Stone et al., Regeneration of Meniscal Cartilage with Use of a Collagen Scaffold, The Journal of Bone and Joint Surgery, Incorporated, Dec. 1997, pp. 1770-1777, vol. 79-A, No. 12.

Suggs et al., Platelet adhesion on a bioresorbable poly (propylene fumarate-co-ethylene glycol) copolymer, Biomaterials 20, 1999, pp. 683-690, Elsevier Science Ltd.

Troxel, Karen S., Delay of Skin Would Contraction by Porous Collagen-GAG Matrices, (Ph.D. Thesis, Massachusetts Institute of Technology), 1994, 1 pp.

Weadock et al., Physical crosslinking of collagen fibers: Comparison of ultraviolet irradiation and dehydrothermal treatment, Journal of Biomedical Materials Research, 1995, pp. 1373-1379, vol. 29.

Witkowski et al., Migration and Healing of Ligament Cells under Inflammatory Conditions, Journal of Orthopaedic Research, The Journal of Bone and Joint Surgery, Inc., 1997, pp. 269-277, vol. 15, No. 2.

Yannas, Ioannis V., Models of Organ Regeneration Processes Induced by Templates, Bioartificial Organs: Science, Medicine and Technology, 1997, pp. 280-293, The New York Academy of Sciences, New York, NY.

Yannas, Ioannis V., Regeneration of Skin and Nerve by Use of Collagen Templates, Collagen, Sep. 23, 2002, pp. 87-115, vol. III, No. 3345.

Yannas et al., Polymeric Template Facilitates Regeneration of Sciatic Nerve Across, The 11th Annual Meeting of the Society for Biomaterials, San Diego, CA, Apr. 25-28, 1985, pp. 146.

Yannas et al., Synthesis and characterization of a model extracellular matrix that induces partial regeneration of adult mammalian skin, Developmental Biology, Proc. Nat'l. Acad. Sci. USA, Feb. 1989. pp. 933-937, vol. 86, No. 3.

Al-Munajjed et al., Development of a collagen calcium-phosphate scaffold as a novel bone graft substitute, Royal College of Surgeons in Ireland, Jan. 1, 2008, 10 pp.

Anseth et al., Photopolymerizable degradable polyanhydrides with osteocompatibility, Nature Biotechnology, Feb. 1999, pp. 156-159, vol. 17.

Arendt et al., Knee Injury Patterns Among Men and Women in Collegiate Basketball and Soccer, The American Journal of Sports Medicine, American Orthopaedic Society for Sports Medicine, 1995, pp. 694-701, Vo. 23, No. 6.

Authorized Officer Athina Nickitas-Etienne, International Preliminary Report on Patentability, International Patent Application No. PCT/US2014/014141, dated May 13, 2014, 9 pp.

Authorized Officer Athina Nickitas-Etienne, International Preliminary Report on Patentability, International Patent Application No. PCT/US2006/004445, dated Feb. 17, 2009, 4 pp.

Authorized Officer Aurore Schneider, International Search Report and the Written Opinion, International Patent Application No. PCT/US2017/040865, dated Oct. 19, 2017, 8 pp.

Authorized Officer Brian Pellegrino, International Search Report, International Patent Application PCT/US2002/023885, dated Sep. 30, 2002, 3 pp.

Authorized Officer Brian Pellegrino, International Preliminary Examination Report, International Patent Application PCT/US2002/023885, dated Jan. 30, 2003, 3 pp.

Authorized Officer Ellen Moyse, International Preliminary Report on Patentability, International Patent Application No. PCT/US2007/001908, dated Jul. 29, 2008, 9 pp.

Authorized Officer Ellen Moyse, International Preliminary Report on Patentability, International Patent Application No. PCT/US2007/021009, dated Jan. 12, 2010, 13 pp.

Authorized Officer Lee W. Wong, International Search Report and the Written Opinion, International Patent Application No. PCT/US2007/001908, dated Sep. 5, 2007, 10 pp.

Authorized Officer Manuel A. Mendez, International Search Report and the Written Opinion, International Patent Application No. PCT/US2006/004445, dated Jun. 13, 2008, 5 pp.

Authorized Officer Monica Lopez Garcia, International Search Report and the Written Opinion, International Patent Application No. PCT/US2007/021009, dated Sep. 1, 2009, 18 pp.

Authorized Officer Ross Heosey, International Search Report and the Written Opinion, International Patent Application No. PCT/US2013/024467, dated Apr. 29, 2013, 12 pp.

Authorized Officer Shawn Lyons, International Search Report and the Written Opinion, International Patent Application No. PCT/US2014/014141, dated May 13, 2014, 14 pp.

Authorized Officer Simin Baharlou, International Preliminary Report on Patentability, International Patent Application No. PCT/US2017/040865, dated Jan. 8, 2019, 6 pp.

Buck, R.C., Regeneration of Tendon, The Journal of Pathology and Bacteriology, 1953, 22 pp., vol. LXVI, No. I.

Chamberlain et al., Early peripheral nerve healing in collagen and silicone tube implants: Myofibroblasts and the cellular response, Biomaterials 19, Elsevier, 1998, pp. 1393-1403.

Chamberlain et al., Collagen-GAG Substrate Enhances the Quality of Nerve Regeneration through Collagen Tubes up to Level of Autograft, Experimental Neurology 154, 1998, pp. 315-329, American Press.

Chamberlain, Lila Jo, Long Term Functional and Morphological Evaluation of Peripheral Nerves Regenerated Through Degradable Collagen Implants, MS Thesis, Massachusetts Institute of Technology, 1998, pp. 2.

Crapo et al., An overview of tissue and whole organ decellularization processes, NIH Public Access, Elsevier, Ltd., Biomaterials, Apr. 2011, pp. 3233-3243.

Cross et al., Dense type I collagen matrices that support cellular remodeling and microfabrication for studies of tumor angiogenesis and vasculogenesis in vitro, Biomaterials, 2010, pp. 8596-8507, Elsevier, Ltd.

Deie et al., High intrinsic healing potential of human anterior cruciate ligament, Acta Orthopaedica Scandinavica, 1995, pp. 28-32, vol. 66(1).

Desrosiers et al., Proliferative and Matrix Synthesis Response of Canine Anterior Cruciate Ligament Fibroblasts Submitted to Combined Growth Factors, Journal of Orthopaedic Research, The Journal of Bone and Joint Surgery, Inc., 1996, pp. 200-208, vol. 14, No. 2.

Dye, Scott F. MD, The Future of Anterior Cruciate Ligament Restoration, Clinical Orthopaedics and Related Research, Apr. 1996, pp. 130-139, vol. 325.

Extended European Search Report, European Patent Application No. 13743583.0, dated Sep. 17, 2015, 7 pp.

Extended European Search Report, European Patent Application No. 06720499.0, Completed Jul. 7, 2009, 7 pp.

Australian Examination Report, Australian Patent Application 2017254864, dated Aug. 31, 2018, 7 pp.

Partial European Search Report, European Patent Application 14745975.4, dated Aug. 26, 2016, 7 pp.

International Preliminary Report on Patentability, PCT/US2013/024467, dated Aug. 5, 2014, 7 pp.

Faryniarz et al., Myofibroblasts in the Healing Lapine Medical Collateral Ligament: Possible Mechanisms of Contraction, Journal of Orthopaedic Research, The Journal of Bone and Joint Surgery, Inc., 1996, pp. 228-238, vol. 14, No. 2.

Ferber, Dan, Lab-Grown Organs Begin to Take Shape, Science, Apr. 1999, 6 pp., The American Association for the Advancement of Science, vol. 284, No. 5413.

Ferber, Dan, Tissue Engineering: From the Lab to the Clinic, Science, Apr. 1999, 2 pp., The American Association for the Advancement of Science, vol. 284, No. 5413.

Ford et al., Autologous Collagen Vocal Fold Injection: A Preliminary Clinical Study, Sep. 1995, 944-948, Laryngoscope 105.

Frank et al., Natural History of Healing in the Repaired Medial Collateral Ligament, Journal of Orthopaedic Research, Orthopaedic Research Society, 1983, pp. 179-188, vol. 1, No. 2.

Geiger, et al., An in Vitro Assay of Anterior Cruciate Ligament (ACL) and Medial Collateral Ligament (MCL) Cell Migration,

(56) References Cited

OTHER PUBLICATIONS

Connective Tissue Research, 1994, pp. 215-224, vol. 30. Gordon and Breach Science Publishers, S.A.

Gerich et al., Gene transfer to the patellar tendon, Knee Surg., Sports Traumatol, Arthroscopy, 1998, pp. 118-123, Springer-Verlag.

Gwinn et al., Relative Gender Incidence of Anterior Cruciate Ligament Injury at a Military Service Academy, 66th Annual Meeting of the American Academy of Orthopaedic Surgeons, Anaheim, CA, 1999, 1 pp., Paper No. 143.

Hefti et al., Healing of the Transected Anterior Cruciate Ligament in the Rabbit, The Journal of Bone and Joint Surgery, Mar. 1991, pp. 373-383, vol. 73-A, No. 3.

Itoh et al., Characterization of CO3AP-collagen sponges using X-ray high-resolution microtomography, Biomaterials, 2004, pp. 2577-2583, vol. 25.

Jackson et al., Biologic remodeling after anterior cruciate ligament reconstruction using a collagen matrix derived from demineralized bone: an experimental study in the goat model, The American Journal of Sports Medicine, Jul.-Aug. 1996, 15 pp., vol. 24, No. 4.

Juncosa-Melvin et al., The Effect of Autologous Mesenchymal Stem Cells on the Biomechanics an Histology of Gel-Collagen Sponge Constructs Used for Rabbit Patellar Tendon Repair, Tissue Engineering, 2006, pp. 370-380, vol. 12.

Kanungo et al., Density-property relationships in mineralized collagen-glycosaminoglycan scaffolds, Aug. 26, 2008, pp. 1006-1018, Acta Biomaterials 5, Elsevier.

Kato et al., Formation of continuous collagen fibres: evaluation of biocompatibility ad mechanical properties, Biomaterials, Apr. 1990, pp. 169-175, vol. 11, Butterworth & Co., Ltd (Publishers).

Kawamoto et al., Selective migration of alpha-smooth muscle actin-positive myofibroblasts toward fibronectin in the Boyden's blindwell chamber, Clinical Science, 1997, pp. 355-362, vol. 93.

Kliment et al., A novel method for accurate collagen and biochemical assessment of pulmonary tissue utilizing one animal, Int. J. Clin. Exp. Pathol., 2011, pp. 349-355.

Louie, Libby K., Effect of a Porous Collagen-Glycosaminoglycan copolymer on Early Tendon Healing in a Novel Animal Model, Jan. 10, 1997, 1 pp., Ph.D. Thesis, Massachusetts Institute of Technology.

Louie et al., Development of a Collagen-GAG Copolymer Implant for the Study of Tendon Regeneration, Materials Research Society Symposium Proceedings, 1994, pp. 19-24, vol. 331.

Louie et al., Healing of Tendon Defects Implanted with a Porous Collagen=GAG Matrix: Histological Evaluation, Tissue Engineering, 1997, pp. 187-195, vol. 3, No. 2.

Marshall et al., The Anterior Ligament Cruciate Ligament: A Technique of Repair and Reconstruction, Clinical Orthopaedics and Related Research, Sep. 1979, pp. 97-106, No. 143.

\* cited by examiner

SUTURES ONLY

SUTURES + HYDROGEL

 
Fig. 6A    Fig. 6B
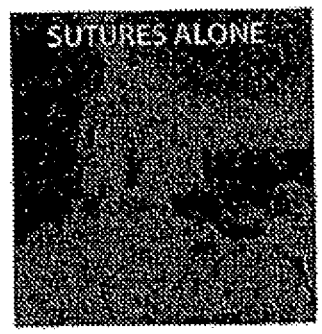 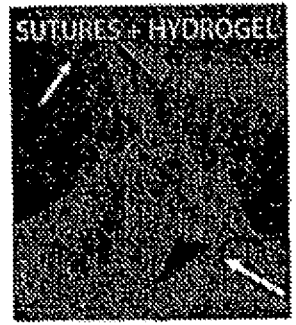
FIG. 7A    FIG. 7B

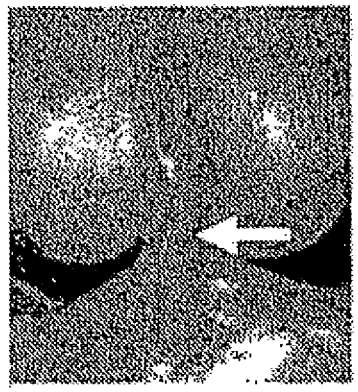
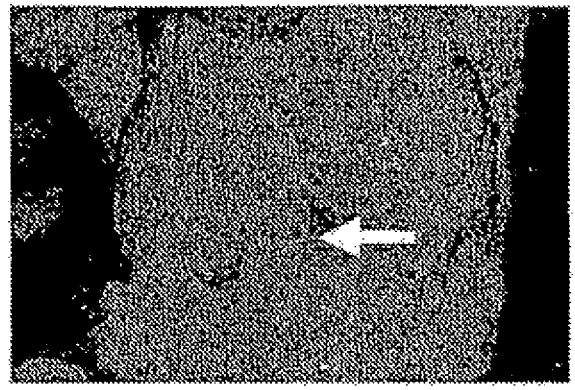
Fig. 8A  Fig. 8B
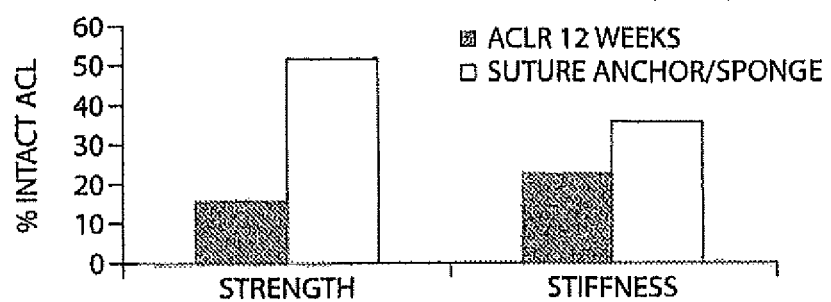
Fig. 9

METHODS AND PROCEDURES FOR LIGAMENT REPAIR

CROSS-REFERENCE TO RELATED APPLICATIONS

This application is a divisional of U.S. application Ser. No. 16/228,196, filed Dec. 20, 2018, which is a continuation of U.S. application Ser. No. 13/461,269, filed May 1, 2012, which is a continuation of U.S. application Ser. No. 12/162,108, filed Mar. 25, 2009, which is a 371 National Stage of International Application No. PCT/US2007/001908 filed on Jan. 25, 2007, which designates the United States, and which claims benefit under 35 U.S.C. § 119(e) of U.S. Provisional Application No. 60/761,951 filed on Jan. 25, 2006, the entire contents of all of which are incorporated herein by reference.

FIELD OF THE INVENTION

The invention relates generally to methods and devices for the repair of a ruptured ligament using a scaffold device.

BACKGROUND OF THE INVENTION

Intra-articular tissues, such as the anterior cruciate ligament (ACL), do not heal after rupture. In addition, the meniscus and the articular cartilage in human joints also often fail to heal after an injury. Tissues found outside of joints heal by forming a fibrin clot, which connects the ruptured tissue ends and is subsequently remodeled to form scar, which heals the tissue. Inside a synovial joint, a fibrin clot either fails to form or is quickly lysed after injury to the knee, thus preventing joint arthrosis and stiffness after minor injury. Joints contain synovial fluid which, as part of normal joint activity, naturally prevent clot formation in joints. This fibrinolytic process results in premature loss of the fibrin clot scaffold and disruption of the healing process for tissues within the joint or within intra-articular tissues.

The current treatment method for human anterior cruciate ligament repair after rupture involves removing the ruptured fan-shaped ligament and replacing it with a point-to-point tendon graft (ACL reconstruction). While this procedure can initially restore gross stability in most patients, longer follow-up demonstrates many post-operative patients have abnormal structural laxity, suggesting the reconstruction may not withstand the physiologic forces applied over time (Dye, 325 Clin. Orthop. 130-139 (1996)). The loss of anterior cruciate ligament function has been found to result in early and progressive radiographic changes consistent with joint deterioration (Hefti et al., 73A(3) J. Bone Joint Surg. 373-383 (1991)), and over 70% of patients undergoing ACL reconstruction develop osteoarthritis at only 14 years after injury (von Porat et al., Ann Rheum Dis. 63(3):269-73 (2004)). As anterior cruciate ligament rupture is most commonly an injury of a young athletes in their teens and twenties, early osteoarthritis in this group has difficult consequences.

SUMMARY OF THE INVENTION

The invention relates, in some aspects, to methods and products that facilitate anterior cruciate ligament regeneration or healing. Thus, in some aspects, the invention is a device for repairing a ruptured ligament having a scaffold configured for repair of a ruptured ligament and an anchor. The scaffold is attached to the anchor with a suture. The suture has at least one free end emerging from the scaffold. The suture and/or anchor may be bioabsorbable and/or synthetic, such as, for instance, polyglactin 910.

In some embodiments, the scaffold is made of protein, such as, for example, a synthetic, bioabsorbable, or a naturally occurring protein. In other embodiments, the scaffold is a lyophilized material. The scaffold may be expandable. In other embodiments, the scaffold may be a sponge, a gel, a solid, or a semi-solid. The scaffold may be pretreated with a repair material. Repair materials include but are not limited to gels, liquids, and hydrogels. The repair material in some embodiments is collagen.

A method of repairing a ruptured ligament is provided according to other aspects of the invention. The method involves inserting a device for repairing a ruptured ligament as described herein into a repair site of the ruptured ligament, attaching the anchor to a bone near the repair site, and attaching the free end of the suture to an end of the ruptured ligament.

A method of repairing a ruptured ligament that involves drilling a hole near a repair site of a ruptured ligament, attaching a suture to the bone through the hole, and attaching a scaffold to the suture to secure the scaffold between the bone and an end of the ruptured ligament is provided in other aspects of the invention.

In some embodiments, both ends of the suture are attached to the end of the ruptured ligament. In other embodiments, the suture is attached to a second bone site by a second anchor.

The scaffold in some embodiments is made from a protein. The protein may be synthetic, bioabsorbable, or a naturally occurring protein. In some embodiments, the scaffold can absorb plasma, blood, or other body fluids.

In other embodiments the scaffold is tubular, semi-tubular, cylindrical, or square. The scaffold is a sponge or a gel in some embodiments. In other embodiments, the scaffold is a semi-solid or, alternatively, a solid.

In yet other embodiments the scaffold is expandable. It may optionally fill the repair site. In some embodiments, the scaffold is bigger than the repair site and in other embodiments the scaffold partially fills the repair site. The scaffold may form around the ligament at the repair site. The scaffold may be pretreated with a repair material, such as a gel or a liquid. In some embodiments, the repair material is a hydrogel. In other embodiments, the repair material is collagen.

In some embodiments, the ligament is ACL and the bone is a femur or a tibia. In some embodiments, the repair is supplemented by forming holes in the surrounding bone to cause bleeding into the repair site.

A method of repairing a ruptured ligament that involves drilling a hole near a repair site of a ruptured ligament and attaching an anchor to the bone through the hole is provided in some aspects of the invention. The method involves attaching an anchor to the bone through the hole where the anchor is attached to a scaffold and the scaffold is secured between the bone and an end of the ruptured ligament.

In some embodiments, the ligament is ACL and the bone is a femur or a tibia. In some embodiments, the anchor is bioabsorbable, metal, plastic, etc. In other embodiments, the anchor is a screw. In certain embodiments, the anchor is attached to the bone by a suture. In some embodiments, the suture is a bioabsorbable, synthetic etc. In other embodiments, the suture is polyglactin 910.

In some embodiments, the scaffold is synthetic, bioabsorbable, or a naturally occurring protein. In certain embodiments, the scaffold can absorb plasma, blood, or other body fluids. In other embodiments, the scaffold is tubular, semi-tubular, cylindrical, or square. In certain embodiments, the scaffold is pretreated with a repair material. In some embodiments, the repair material is a gel or a liquid. In other embodiments, the repair material is hydrogel. In some embodiments, the repair material is collagen.

In some embodiments, the repair is supplemented by forming holes in the surrounding bone to cause bleeding into the repair site. In certain embodiments, the scaffold is expandable. It may optionally fill the repair site. In some embodiments, the scaffold is bigger than the repair site and in other embodiments the scaffold partially fills the repair site. The scaffold may form around the ligament at the repair site. The scaffold may be pretreated with a repair material, such as a gel or a liquid. In some embodiments, the repair material is a hydrogel. In other embodiments, the repair material is collagen.

In some embodiments, the scaffold is a sponge. In certain embodiments, the scaffold is a gel. In other embodiments, the scaffold is a semi-solid. In some embodiments, the scaffold is a solid.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

FIG. 1A is a diagrammatic representation of a torn anterior cruciate ligament. FIG. 1B is a diagrammatic representation of a scaffold device having an anchor and attached sutures. FIG. 1C is a diagrammatic representation of a scaffold device implanted into a repair site around a ruptured ACL.

FIG. 2A is a diagrammatic representation of a suture anchor inserted into a bone. 2B is a diagrammatic representation of a drill hole in a bone and sutures attached to the opposite surface of the bone. FIG. 2C is a diagrammatic representation of a staple affixing a suture into a notch. FIG. 2D is a diagrammatic representation of an anchor with a central hole to allow bone marrow bleeding to flow into the attached scaffold. FIG. 2E is a diagrammatic representation of an anchor with a scaffold sponge swaged directly onto it.

FIG. 3A is a diagrammatic representation of a suture attached through a drill hole in a bone. FIG. 3B is a diagrammatic representation of an anchor inserted into a bone.

FIG. 4A is a MRI image of ACL treated with sutures alone. FIG. 4B is a MRI image of ACL treated with sutures+hydrogel. FIG. 4C is a diagrammatic representation of ACL with suture only. FIG. 4D is a diagrammatic representation of ACL with sutures+hydrogel.

FIGS. 5A, 5C. 5E is MRI image of ACL treated with suture alone in the early (FIG. 5A), mid (FIG. 5C) or late stage (FIG. 5E). FIG. 5B is a MRI image of ACL treated with suture+hydrogel in the early (FIG. 5A), mid (FIG. 5D) or late stage (FIG. 5F).

FIG. 6A-6B. FIG. 6A is a MRI image of ACL scar treated with suture alone. FIG. 6B is a MRI image of ACL scar treated with suture+hydrogel.

FIG. 7A-7B. FIG. 7A is a photographic representation of ACL treated with suture alone. FIG. 7B is a photographic representation of ACL treated with suture+hydrogel.

FIG. 8A-8B. FIG. 8A is a MRI image of intact ACL. FIG. 8B is an ACL repaired with suture, anchor and sponge.

FIG. 9 is a graph depicting biomechanical properties of Suture Anchor/Sponge Repair vs the current standard of care for ACL injuries (ACL Reconstruction or ACLR) at 3 months in vivo.

DETAILED DESCRIPTION OF THE INVENTION

Aspects of the invention relate to devices and methods for repairing a ruptured ligament. A device of the invention for the repair of a ruptured ligament includes a scaffold which is configured for the repair of a ruptured ligament, an anchor and may include a suture. The scaffold allows the subject's body to develop a network of capillaries, arteries, and veins. Well-vascularized connective tissues heal as a result of migration of fibroblasts into the scaffold. A device of the invention provides a connection between a ruptured ligament, or forms around a torn ligament, and promotes the repair of the ruptured or torn ligament while maintaining the integrity and structure of the ligament.

The device of the invention provides a three-dimensional (3-D) scaffold for repairing a ruptured or torn ligament. The scaffold provides a connection between the ruptured ends of the ligament and fibers, or forms around a torn ligament, after injury, and encourages the migration of appropriate healing cells to form scar and new tissue in the scaffold. The scaffold is a bioengineered substitute for a fibrin clot and is implanted, for example, between the ruptured ends of the ligament fascicles, or placed around a torn ligament. This substitute scaffold is designed to stimulate cell proliferation and extracellular matrix production in the gap between the ruptured ends of the ligament or the tear in the ligament, thus facilitating healing and regeneration.

Methods and devices of the invention may be used to treat either intra-articular or extra-articular injuries in a subject. Intra-articular injuries include, but are not limited to, meniscal tears, ligament tears and cartilage lesion. Extra-articular injuries include, but are not limited to, the ligament, tendon or muscle. Thus, the methods of the invention may be used to treat injuries to the anterior cruciate ligament, the meniscus, labrum, for example glenoid labrum and acetabular labrum, cartilage, and other tissues exposed to synovial fluid after injury.

An injury may be a torn or ruptured ligament. A torn ligament is one where the ligament remains connected but has been damaged causing a tear in the ligament. The tear may be of any length or shape. A ruptured ligament is one where the ligament has been completely severed providing two separate ends of the ligament. A ruptured ligament may provide two ligament ends of similar or different lengths. The rupture may be such that a ligament stump is formed at one end.

Figure 1A:
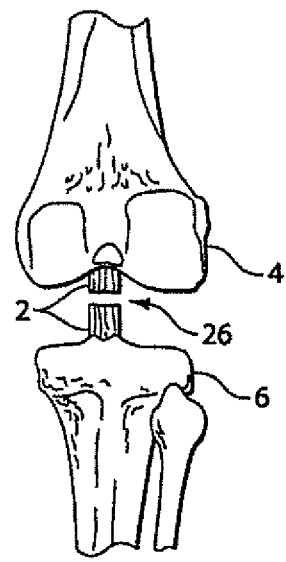
FIGS. 1A-1C.

An example of a ruptured anterior cruciate ligament is depicted in FIG. 1A. The anterior cruciate ligament (ACL)

(2) is one of four strong ligaments that connects the bones of the knee joint. The function of the ACL is to provide stability to the knee and minimize stress across the knee joint. It restrains excessive forward movement of the lower leg bone, the tibia (6), in relation to the thigh bone, the femur (4), and limits the rotational movements of the knee. An anterior cruciate ligament (2) is ruptured such that it no longer forms a connection between the femur bone (4) and the tibia bone (6). The resulting ends of the ruptured ACL may be of any length. The ends may be of a similar length, or one end may be longer in length than the other.

A scaffold of the device of the invention can be any shape that is useful for implantation into a subject. The scaffold, for instance, can be tubular, semi-tubular, cylindrical, including either a solid cylinder or a cylinder having hollow cavities, a tube, a flat sheet rolled into a tube so as to define a hollow cavity, liquid, an amorphous shape which conforms to that of the repair space, a "Chinese finger trap" design, a trough shape, or square. Other shapes suitable for the scaffold of the device as known to those of ordinary skill in the art are also contemplated in the invention.

In aspects of the invention, a device for repairing a ruptured or torn ligament includes a scaffold and an anchor, such that the scaffold is configured for repair. A scaffold that is configured for repair is one that is capable of being inserted into an area requiring repair and promotes regeneration of the ligament. A scaffold of the invention is capable of insertion into a repair site and either forming a connection between the ends of a ruptured ligament, or forming around a torn ligament such that, in either case, the integrity and structure of the ligament is maintained. Regeneration offers several advantages over reconstruction, previously used in ligament repair, including maintenance of the complex insertion sites and fan-shape of the ligament, and preservation of remaining proprioceptive fibers within the ligament substance.

Figure 1B:
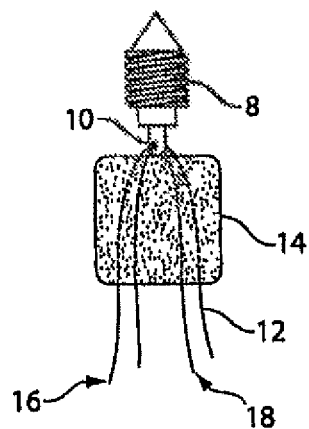
Figure 1C:
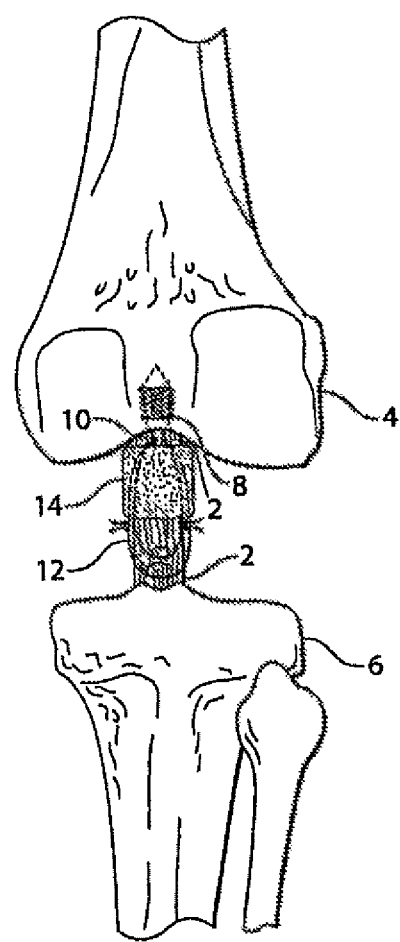
Figure 2A:
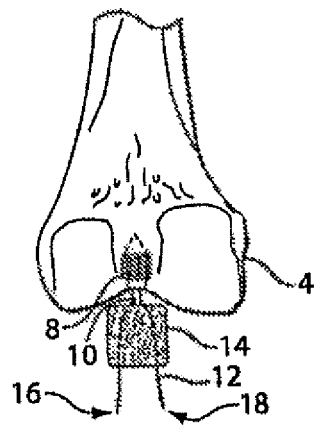
FIGS. 2A-2E. Diagrammatic representation of a method for inserting a scaffold device into bone.
Figure 2B:
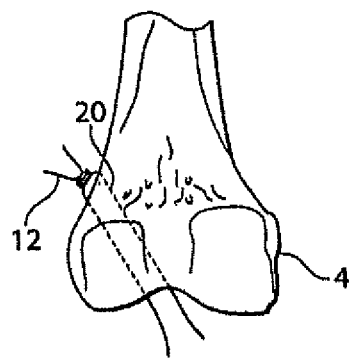
Figure 2C:
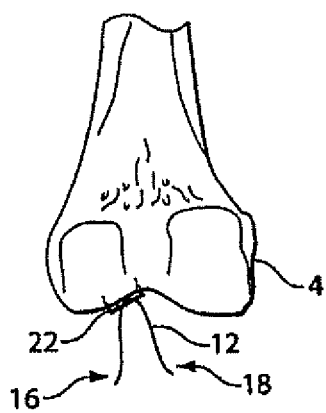
Figure 2D:
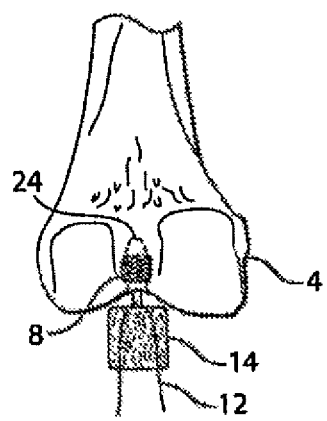
Figure 2E:
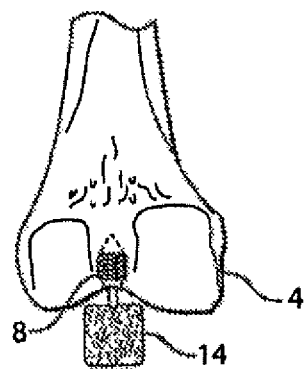
Figure 3A:
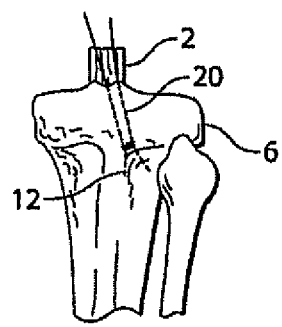
FIGS. 3A-3B. Diagrammatic representation of a method for distal fixation of a scaffold device to bone.
Figure 3B:
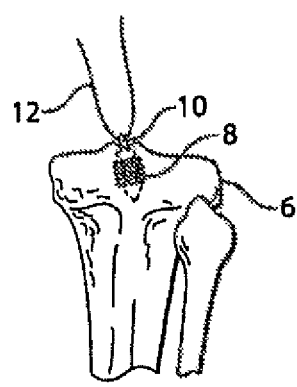
Figure 4A:
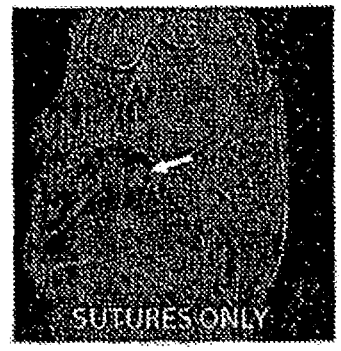
FIGS. 4A-4D.
Figure 4B:
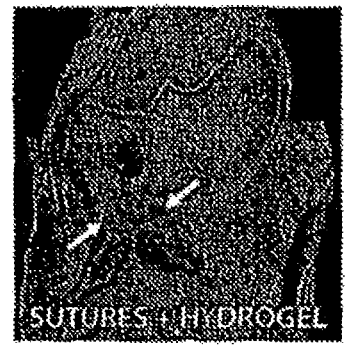
Figure 4C:
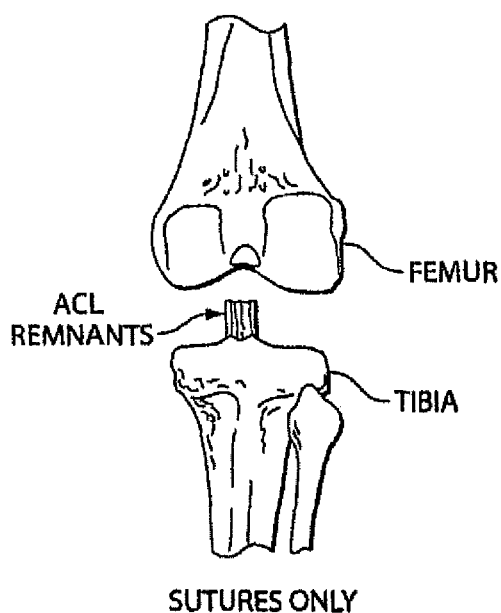
Figure 4D:
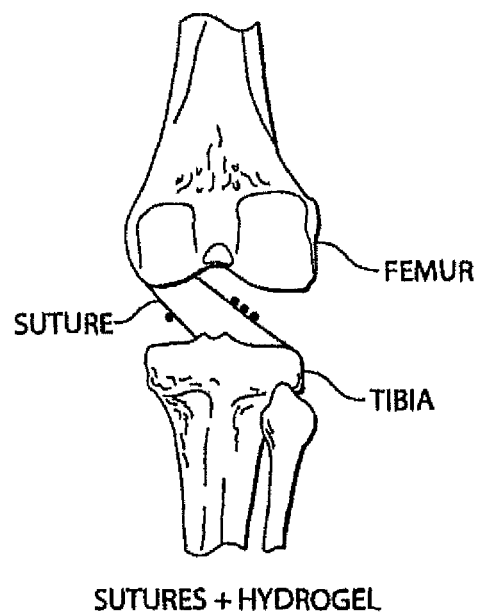
Figure 5A:
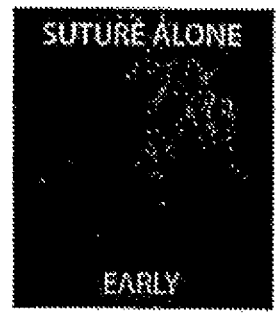
FIGS. 5A-5F.
Figure 5B:
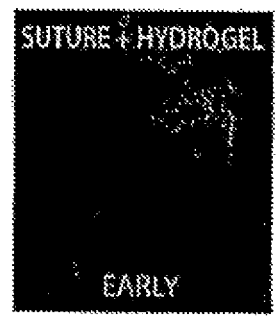
Figure 5C:
Figure 5D:
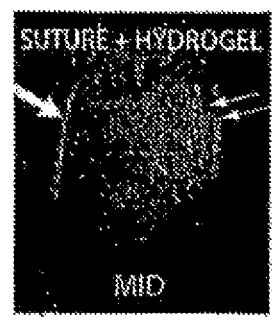
Figure 5E:
Figure 5F:
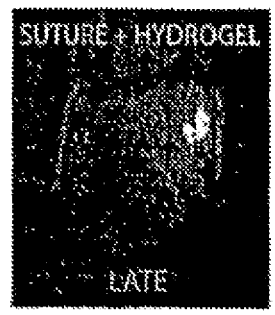

Examples of devices and systems useful according to the invention are depicted in FIGS. 1-3. An example of a device is depicted in FIGS. 1B and 1C. For example, a scaffold (14) is attached to a suture (12) and an anchor (8). The anchor (8) may, as shown in FIGS. 1B and 1C, be attached to the suture (12) through an eyelet (10) of the anchor (8). The anchor (8) is attached (12) into a bone such as the femur (4) or a tibia (6).

A scaffold (14) may function either as an insoluble or biodegradable regulator of cell function or simply as a delivery vehicle of a supporting structure for cell migration or synthesis. Numerous matrices made of either natural or synthetic components have been investigated for use in ligament repair and reconstruction. Natural matrices are made from processed or reconstituted tissue components (such as collagens and GAGs). Because natural matrices mimic the structures ordinarily responsible for the reciprocal interaction between cells and their environment, they act as cell regulators with minimal modification, giving the cells the ability to remodel an implanted material, which is a prerequisite for regeneration.

Synthetic matrices are made predominantly of polymeric materials. Synthetic matrices offer the advantage of a range of carefully defined chemical compositions and structural arrangements. Some synthetic matrices are not degradable. While the non-degradable matrices may aid in repair, non-degradable matrices are not replaced by remodeling and therefore cannot be used to fully regenerate ligament. It is also undesirable to leave foreign materials permanently in a joint due to the problems associated with the generation of wear particles, thus degradable materials are preferred for work in regeneration. Degradable synthetic scaffolds can be engineered to control the rate of degradation.

A scaffold is preferably made of a compressible, resilient material which has some resistance to degradation by synovial fluid. Synovial fluid as part of normal joint activity, naturally prevents clot formation. This fibrinolytic process would result in the premature degradation of the scaffold and disrupt the healing process of the ligament. The material may be either permanent or biodegradable material, such as polymers and copolymers. The scaffold can be composed, for example, of collagen fibers, collagen gel, foamed rubber, natural material, synthetic materials such as rubber, silicone and plastic, ground and compacted material, perforated material, or a compressible solid material.

A scaffold may be a solid material such that its shape is maintained, or a semi-solid material capable of altering its shape and or size. A scaffold may be made of expandable material allowing it to contract or expand as required. The material can be capable of absorbing plasma, blood, other body fluids, liquid, hydrogel, or other material the scaffold either comes into contact with or is added to the scaffold.

A scaffold material can be protein, lyophilized material, or any other suitable material. A protein can be synthetic, bioabsorbable or a naturally occurring protein. A protein includes, but is not limited to, fibrin, hyaluronic acid, elastin, extracellular matrix proteins, or collagen. A scaffold material may be plastic or self-assembling peptides. A scaffold material may incorporate therapeutic proteins including, but not limited to, hormones, cytokines, growth factors, clotting factors, anti-protease proteins (e.g., alpha1-antitrypsin), angiogenic proteins (e.g., vascular endothelial growth factor, fibroblast growth factors), antiangiogenic proteins (e.g., endostatin, angiostatin), and other proteins that are present in the blood, bone morphogenic proteins (BMPs), osteoinductive factor (IFO), fibronectin (FN), endothelial cell growth factor (ECGF), cementum attachment extracts (CAE), ketanserin, human growth hormone (HGH), animal growth hormones, epidermal growth factor (EGF), interleukin-1 (IL-1), human alpha thrombin, transforming growth factor (TGF-beta), insulin-like growth factor (IGF-1), platelet derived growth factors (PDGF), fibroblast growth factors (FGF, bFGF, etc.), and periodontal ligament chemotactic factor (PDLGF), for therapeutic purposes. A lyophilized material is one that is capable of swelling when liquid, gel or other fluid is added or comes into contact with it.

Many biological materials are available for making the scaffold, including collagen compositions (either collagen fiber or collagen gel), compositions containing glycosaminoglycan (GAG), hyaluronan compositions, and various synthetic compositions. Collagen-glycosaminoglycan (CG) copolymers have been used successfully in the regeneration of dermis and peripheral nerve. Porous natural polymers, fabricated as sponge-like and fibrous scaffolds, have been investigated as implants to facilitate regeneration of selected musculoskeletal tissues including ligaments. A scaffold, such as a sponge scaffold, may also be made from tendon (xenograft, allograft, autograft) or ligament or skin or other connective tissue which could be in the native state or processed to facilitate cell ingrowth or other biologic features.

In aspects of the invention, a scaffold is composed of a sponge or sponge-like material. A sponge scaffold may be absorbable or nonabsorbable. A sponge scaffold may be collagen, elastin, extracellular matrix protein, plastic, or self-assembling peptides. A sponge scaffold may be hydrophillic. A sponge scaffold is capable of compression and expansion as desired. For example, a sponge scaffold may be compressed prior to or during implantation into a repair site. A compressed sponge scaffold allows for the sponge scaffold to expand within the repair site. A sponge may be lyophilized and/or compressed when placed in the repair site and expanded once in place. The expansion of a sponge scaffold may occur after contact with blood or other fluid in the repair site or added to the repair site. A sponge scaffold may be porous. A sponge scaffold may be saturated or coated with a liquid, gel, or hydrogel repair material prior to implantation into a repair site. Coating or saturation of a sponge scaffold may ease implantation into a relatively undefined defect area as well as help to fill a particularly large defect area. A sponge scaffold may be composed of collagen. In a preferred embodiment, a sponge scaffold is treated with hydrogel. Examples of scaffolds and repair materials useful according to the invention are found in U.S. Pat. No. 6,964,685 and U.S. Patent Application Nos. 2004/0059416 and 2005/0261736, the entire contents of each are herein incorporated by reference.

An important subset of natural matrices are those made predominantly from collagen, the main structural component in ligament. Collagen can be of the soluble or the insoluble type. Preferably, the collagen is soluble, e.g., acidic or basic. For example, the collagen can be type I, II, III, IV, V, IX or X. Preferably the collagen is type I. More preferably the collagen is soluble type I collagen. Type I collagen is the predominant component of the extracellular matrix for the human anterior cruciate ligament and provides an example of a choice for the basis of a bioengineered scaffold. Collagen occurs predominantly in a fibrous form, allowing design of materials with very different mechanical properties by altering the volume fraction, fiber orientation, and degree of cross-linking of the collagen. The biologic properties of cell infiltration rate and scaffold degradation may also be altered by varying the pore size, degree of cross-linking, and the use of additional proteins, such as glycosaminoglycans, growth factors, and cytokines. In addition, collagen-based biomaterials can be manufactured from a patient's own skin, thus minimizing the antigenicity of the implant (Ford et al., 105 Laryngoscope 944-948 (1995)).

A device of the invention may also include one or more anchors. An anchor is a device capable of insertion into a bone such that it forms a stable attachment to the bone. In some instances, the anchor is capable of being removed from the bone if desired. An anchor may be conical shaped having a sharpened tip at one end and a body having a longitudinal axis. The body of an anchor (8) may increase in diameter along its longitudinal axis. The body of an anchor may include grooves suitable for screwing the anchor into position. For example, as depicted in FIG. 1C, the anchor (8) is screwed into the femur bone (4). An anchor may include an eyelet (10) at the base of the anchor body through which one or more sutures may be passed. The eyelet (10) may be oval or round and may be of any size suitable to allow one or more sutures to pass through and be held within the eyelet (10).

An anchor may be attached to a bone by physical or mechanical methods as known to those of ordinary skill in the art. An anchor includes, but is not limited to, a screw, a barb, a helical anchor, a staple, a clip, a snap, a rivet, or a crimp-type anchor. The body of an anchor may be varied in length. Examples of anchors, include but are not limited to, IN-FAST™ Bone Screw System (Influence, Inc., San Francisco, Calif.), IN-TAC™ Bone Anchor System (Influence, Inc., San Francisco, Calif.), Model 3000 AXYALOOP™ Titanium Bone Anchor (Axya Medical Inc., Beverly, Mass.), OPUS MAGNUM® Anchor with Inserter (Opus Medical, Inc., San Juan Capistrano, Calif.), ANCHRON™, HEXALON™, TRINION™ (all available from Inion Inc., Oklahoma City, Okla.) and TwinFix AB absorbable suture anchor (Smith & Nephew, Inc., Andover, Mass.). Anchors are available commercially from manufacturers such as Influence, Inc., San Francisco, Calif., Axya Medical Inc., Beverly, Mass., Opus Medical, Inc., San Juan Capistrano, Calif., Inion Inc., Oklahoma City, Okla., and Smith & Nephew, Inc., Andover, Mass.

An anchor may be attached directly to a scaffold where the anchor is swaged directly onto the scaffold. FIG. 2E depicts such an example. The anchor (8) is attached directly to the scaffold (14) by its base end and the anchor (8) is attached to the femur (4) by its sharpened end.

An anchor may be attached indirectly to a scaffold using a suture to secure it in position. FIG. 2A depicts such an example. A suture (12) is passed through the eyelet (10) of the anchor (8) and held within the eyelet (10) to attach the scaffold (14). The first end (16) and the second end (18) of the suture are free and emerge from the scaffold (14). The anchor (8) is attached to the femur (4) by its sharpened end.

An anchor may be composed of a non-degradable material, such as metal, for example titanium 316 LVM stainless steel, CoCrMo alloy, or Nitinol alloy, or plastic. An anchor is preferably bioabsorbable such that the subject is capable of breaking down the anchor and absorbing it. Examples of bioabsorbable material include, but are not limited to, MONOCRYL (poliglecaprone 25), PDS II (polydioxanone), surgical gut suture (SGS), gut, coated VICRYL (polyglactin 910, polyglactin 910 braided), human autograft tendon material, collagen fiber, POLYSORB, poly-L-lactic acid (PLLA), polylactic acid (PLA), polysulfone, polylactides (Pla), racemic form of polylactide (D,L-Pla), poly(L-lactide-co-D,L-lactide), 70/30 poly(L-lactide-co-D,L-lactide), polyglycolides (PGa), polyglycolic acid (PGA), polycaprolactone (PCL), polydioxanone (PDS), polyhydroxyacids, and resorbable plate material (see e.g. Orthopedics, October 2002, Vol. 25, No. 10/Supp.). The anchor may be bioabsorbed over a period of time which includes, but is not limited to, days, weeks, months or years.

An anchor may have a central hole (24) through which fluids, such as blood, may pass. The hole (24) may allow such fluids to flow onto the attached scaffold. FIG. 2D depicts such an example. The anchor (8) is attached to the femur (4) and includes a central hole (24) through which blood can pass. Blood is able to pass through the central hole (24) in the anchor (8) and onto the scaffold (14) which absorbs the blood.

In aspects of the invention, an anchor (8) may be attached to a scaffold (14) using a suture (12). FIG. 1B illustrates an example of an anchor attached to a scaffold using a suture. A suture (12) is passed through the eyelet (10) of an anchor (8) such that the anchor (8) is attached to the scaffold (14) by the suture (12). The suture (12) has at least one free end. In some embodiments, a suture has two free ends, a first end (16) and a second end (18).

A suture (12) is preferably bioabsorbable, such that the subject is capable of breaking down the suture and absorbing it, and synthetic such that the suture may not be from a natural source. A suture (12) may be permanent such that the subject is not capable of breaking down the suture and the suture remains in the subject. A suture (12) may be rigid or stiff, or may be stretchy or flexible. A suture (12) may be round in shape and may have a flat cross section. Examples of sutures include, but are not limited to, VICRYL™ polyglactin 910, PANACRYL™ absorbable suture, ETHI- BOND® EXCEL polyester suture, PDS® polydioxanone suture and PROLENE® polypropylene suture. Sutures are available commercially from manufacturers such as MITEK PRODUCTS division of ETHICON, INC. of Westwood, Mass.

A suture (12) may be attached to one or both ends of a ruptured ligament by its first end (16) and/or its second end (18). FIG. 1C illustrates an example of a device of the invention inserted into a repair site of a ruptured ligament. A suture (12) is passed through the eyelet (10) of the anchor and the first end (16) and second end (18) are tied to the ends of the distal ACL (2). The anchor (8) is attached to the femur (4) by its sharpened end. The scaffold (14) attached to the anchor (8) by the suture (12) is held in position in the repair site (26). The anchor (8) may be attached to either the tibia bone (6) or the femur bone (4) to secure the scaffold (14) in position.

A staple (22) is a type of anchor having two arms that are capable of insertion into a bone. In some instances, the arms of the staple fold in on themselves when attached to a bone or in some instances when attached to other tissue. A staple may be composed of metal, for example titanium or stainless steel, plastic, or any biodegradable material. A staple includes but is not limited to linear staples, circular staples, curved staples or straight staples. Staples are available commercially from manufacturers such as Johnson & Johnson Health Care Systems, Inc. Piscataway, N.J., and Ethicon, Inc., Somerville, N.J. A staple may be attached using any staple device known to those of ordinary skill in the art, for example, a hammer and staple setter (staple holder).

In some embodiments, a staple may be used to hold the suture securely in position. A suture may be attached to a bone using a staple as depicted in FIG. 2C. A suture (12) is held in place in the femur (4) with a staple (22) such that the first end (16) and the second end (18) of the suture (12) are free.

Aspects of the invention relate to methods of repairing a ruptured or torn ligament. In some embodiments, a device of the invention is inserted into a repair site of the ruptured or torn ligament. In certain embodiments, a hole is drilled into a bone at or near a repair site of a ruptured or torn ligament and a suture is attached through the hole to the bone.

A repair site (26) is the area around a ruptured or torn ligament (2) into which a device of the invention may be inserted. A device of the invention may be placed into a repair site (26) area during surgery using techniques known to those of ordinary skill in the art. A scaffold (14) of the invention can either fill the repair site (26) or partially fill the repair site (26). A scaffold (14) can partially fill the repair site (26) when inserted and expand to fill the repair site (26) in the presence of blood, plasma or other fluids either present within the repair site (26) or added into the repair site (26).

A scaffold (14) may form around a ruptured or torn ligament (2) at the repair site (26). For example, a scaffold (14) may be formed into a tube shape and wrapped around a ligament, a scaffold (14) may be positioned behind the ligament such that the ligament is held within the scaffold (14), or a scaffold (14) may be a "Chinese finger trap" design where one end is placed over a stump of a ruptured ligament and the second end placed over the other end of the ruptured ligament.

Aspects of the invention provide methods of repairing a ruptured ligament (2) involving drilling a hole (20) at or near a repair site (26) of a ruptured ligament (2). A bone at or near a repair site is one that is within close proximity to the repair site and can be utilized using the methods and devices of the invention. For example, a bone at or near a repair site of a torn anterior cruciate ligament is a femur (4) bone and/or a tibia (6) bone. A hole can be drilled into a bone using a device such as a Kirschner wire (for example a small Kirschner wire) and drill, or microfracture pics or awls. One or more holes may be drilled into a bone surrounding a repair site to promote bleeding into the repair site. The repair can be supplemented by drilling holes into the surrounding bone to cause bleeding. Encouraging bleeding into the repair site may promote the formation of blood clots and enhance the healing process of the injury.

A hole (20) may be drilled into a bone on the opposite side to the repair site (26). A suture (12) may be passed through the hole (20) in the bone and attached to the bone. A scaffold (14) is attached to the suture (12) to secure the scaffold (14) between the bone and an end of a ruptured ligament (2). A ruptured ligament (2) provides two ends of the ligament that were previously connected. A scaffold (14) may be attached to one or both ends (16, 18) of a ruptured ligament (2) by one or more sutures (12). A suture (12) may be attached to a second bone site at or near the repair site. The suture may be attached to the second bone using a second anchor (8).

An example of such a method is depicted in FIG. 2B. A hole is drilled (20) into the opposite side of the femur bone (4). The suture (12) is attached to the opposite side of the femur bone (4) using the first end (16) and the second end (18) through the hole (20).

Another example is depicted in FIG. 3A. A hole (20) is drilled into the tibia (6) near the end of the ruptured ligament (2) and a suture is attached to the tibia (6) through the hole (20).

A scaffold of the device can be pretreated with a repair material prior to implantation into a subject. The scaffold may be soaked in a repair material prior to or during implantation into a repair site. The repair material may be injected directly into the scaffold prior to or during implantation. The repair material may be injected within a tubular scaffold at the time of repair. Repair material includes, but is not limited to, a gel, for example a hydrogel, a liquid, or collagen. A liquid includes any material capable of forming an aqueous material, a suspension or a solution. A repair material may include additional materials, such as growth factors, antibiotics, insoluble or soluble collagen (in fibrous, gel, sponge or bead form), a cross-linking agent, thrombin, stem cells, a genetically altered fibroblast, platelets, water, plasma, extracellular proteins and a cell media supplement. The additional repair materials may be added to affect cell proliferation, extracellular matrix production, consistency, inhibition of disease or infection, tonicity, cell nutrients until nutritional pathways are formed, and pH of the repair material. All or a portion of these additional materials may be mixed with the repair material before or during implantation, or alternatively, the additional materials may be implanted proximate to the defect area after the repair material is in place.

In certain embodiments, a repair material may include collagen and platelets. In some embodiments, platelets are derived from the subject to be treated. In other embodiments, platelets are derived from a donor that is allogeneic to the subject. In certain embodiments, platelets may be obtained as platelet rich plasma (PRP). In a non-limiting example, platelets may be isolated from a subject's blood using techniques known to those of ordinary skill in the art. As an example, a blood sample may be centrifuged at 700 rpm for 20 minutes and the platelet-rich plasma upper layer removed. Platelet density may be determined using a cell count as known to those of ordinary skill in the art. The platelet rich plasma may be mixed with collagen and used as a scaffold. The platelet rich plasma may be mixed with any one or more of the scaffold materials of the invention.

An example of a gel is a hydrogel. A hydrogel is a substance that is formed when an organic polymer (natural or synthetic) is crosslinked via covalent, ionic, or hydrogen bonds to create a three-dimensional open-lattice structure which entraps water molecules to form a gel. A polymer may be crosslinked to form a hydrogel either before or after implantation into a subject. For instance, a hydrogel may be formed in situ, for example, at a repair site. In certain embodiments, a polymer forms a hydrogel within the repair site upon contact with a crosslinking agent. Naturally occurring and synthetic hydrogel forming polymers, polymer mixtures and copolymers may be utilized as hydrogel precursors. See for example, U.S. Pat. No. 5,709,854. In certain embodiments, a hydrogel is a gel and begins setting immediately upon mixture and takes approximately 5 minutes to sufficiently set before closure of the defect and surgery area. Setting time may vary depending on the mixture of gel used and environmental factors.

For instance, certain polymers that can form ionic hydrogels which are malleable may be used to form the hydrogel. For example, a hydrogel can be produced by cross-linking the anionic salt of alginic acid, a carbohydrate polymer isolated from seaweed, with calcium cations, whose strength increases with either increasing concentrations of calcium ions or alginate. Modified alginate derivatives, for example, which have an improved ability to form hydrogels or which are derivatized with hydrophobic, water-labile chains, e.g., oligomers of $\epsilon$-caprolactone, may be synthesized. Additionally, polysaccharides which gel by exposure to monovalent cations, including bacterial polysaccharides, such as gellan gum, and plant polysaccharides, such as carrageenans, may be crosslinked to form a hydrogel. Additional examples of materials which can be used to form a hydrogel include polyphosphazines and polyacrylates, which are crosslinked ionically, or block copolymers such as PLURONICS™ (polyoxyalkylene ether) or TETRONICS™ (nonionic polymerized alkylene oxide), polyethylene oxide-polypropylene glycol block copolymers which are crosslinked by temperature or pH, respectively. Other materials include proteins such as fibrin, polymers such as polyvinylpyrrolidone, hyaluronic acid and collagen. Polymers such as polysaccharides that are very viscous liquids or are thixotropic and form a gel over time by the slow evolution of structure, are also useful.

Another example of a gel is hyaluronic acid. Hyaluronic acid, which forms an injectable gel with a consistency like a hair gel, may be utilized. Modified hyaluronic acid derivatives are particularly useful. Hyaluronic acid is a linear polysaccharide. Many of its biological effects are a consequence of its ability to bind water, in that up to 500 ml of water may associate with 1 gram of hyaluronic acid. Esterification of hyaluronic acid with uncharged organic moieties reduces the aqueous solubility. Complete esterification with organic alcohols such as benzyl renders the hyaluronic acid derivatives virtually insoluble in water, these compounds then being soluble only in certain aprotic solvents. When films of hyaluronic acid are made, the films essentially are gels which hydrate and expand in the presence of water.

A gel may be provided in pharmaceutical acceptable carriers known to those skilled in the art, such as saline or phosphate buffered saline. Such carriers may routinely contain pharmaceutically acceptable concentrations of salt, buffering agents, preservatives, compatible carriers, supplementary immune potentiating agents such as adjuvants and cytokines and optionally other therapeutic agents.

As used herein, the term "pharmaceutically acceptable" means a non-toxic material that does not interfere with the effectiveness of the biological activity of the scaffold material or repair material. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term "carrier" denotes an organic or inorganic ingredient, natural or synthetic, with which the scaffold material is combined to facilitate the application. The components of the pharmaceutical compositions also are capable of being co-mingled with the device of the present invention, and with each other, in a manner such that there is no interaction which would substantially impair the desired pharmaceutical efficacy.

The devices of the invention may be used in surgical procedures. The following is an example of a surgical procedure which may be performed using the devices and methods of the invention. The affected extremity is prepared and draped in the standard sterile fashion. A tourniquet may be used if indicated. Standard arthroscopy equipment may be used. After diagnostic arthroscopy is performed, and the intra-articular lesion identified and defined, the tissue ends are pretreated, either mechanically or chemically, and the scaffold introduced into the tissue defect. The scaffold is then bonded to the surrounding tissue using the methods described herein. This can be done by the addition of a chemical agent or a physical agent such ultraviolet light, a laser, or heat. The scaffold may be reinforced by placement of sutures or clips. The arthroscopic portals can be closed, and a sterile dressing placed. The post-operative rehabilitation is dependent on the joint affected, the type and size of lesion treated, and the tissue involved.

The device of the invention may be used with arthroscopic equipment. The device of the invention may be used by insertion through an open incision. The scaffold is compressible to allow introduction through arthroscopic portals, incisions and equipment. The scaffold can also be pre-treated in antibiotic solution prior to implantation.

A subject includes, but is not limited to, any mammal, such as human, non-human primate, mouse, rat, dog, cat, horse or cow. In certain embodiments, a subject is a human.

The invention also includes in some aspects kits for repair of ruptured or torn ligaments. A kit may include a scaffold of the invention having at least one anchor attached to the scaffold and instructions for use. The scaffold may further include one or more sutures that attach an anchor to the scaffold. A kit may further include a container that contains a repair material as described herein.

EXAMPLES

Example 1

Bilateral ACL transections were performed in six animals and repaired with a four stranded, absorbable suture repair using a variation of the Marshall technique. For each animal, one of the repairs was augmented with placement of a collagen-platelet rich hydrogel at the ACL transection site, while the contralateral knee had suture repair alone. No post-operative immobilization was used. The animals survived for four weeks and then underwent in vivo magnetic resonance imaging followed by euthanasia and immediate biomechanical testing. Six control knees with intact ACLs from three additional 30 kg pigs were also tested biomechanically as an intact ACL control group.

The supplementation of suture repair with a collagen-platelet rich hydrogel resulted in formation of a large scar mass in the region of the ACL which was perfused by the injection of IV gadolinium, suggesting the formation of a vascularized repair tissue in the ACL defect. Despite suture resorption during the in vivo time course, load at yield, stiffness and displacement at yield all improved when collagen-platelet rich hydrogel was used to augment the suture repairs. The use of suture repair alone, or suture repair augmented with a collagen-platelet poor hydrogel did not show improvement in any of these parameters.

Biomechanical healing of the porcine ACL after complete transection and suture repair can be enhanced at an early time point with use of a collagen-platelet rich hydrogel placed in the wound site at the time of primary repair.

Developing a technique for primary repair of the ACL may change the focus of treatment of this injury from resection and reconstruction toward repair and regeneration.

Example 2

Experimental Design:

Seven 30 kg Yorkshire pigs underwent bilateral ACL transection and suture repair. Five of the animals were treated on one side with suture repair on one side and suture repair augmented with collagen-platelet rich plasma containing an average of 954K+/−93K platelets/mm$^3$ on the contralateral side (n=5). An additional two animals had suture repair on one side and suture repair augmented with collagen-platelet poor plasma (n=2) with a platelet counts less than 20K/mm$^3$ on the contralateral side (n=5). Sides were randomized to suture alone and augmented repair. All outcomes were measured after four weeks in vivo. Just prior to euthanasia, the animals had in vivo MRI of both knees with gadolinium contrast to assess perfusion of the ACL wound site. Immediately after euthanasia, the knees were harvested and ex vivo MRI performed, followed immediately by biomechanical testing of the ACL complex as previously described (Murray, M. M.; Spindler, K. P.; Devin, C.; Snyder, R. B.; Muller, J.; Ballard, P.; Nanney, L. B.; and Zurakowski, D.: Healing of an intra-articular tissue defect using a stabilized provisional scaffold. *Journal of Bone & Joint Surgery—American Volume*, submitted for publication, 2005). Intact ACLs (n=6) were used as a control group for the biomechanical studies.

Manufacture of Acid Soluble Collagen Used in the Hydrogels:

Rat tails were obtained from control breeder rats undergoing euthanasia. The rat tail tendons were sterilely harvested, minced, and solubilized in an acidified pepsin solution to obtain the acid soluble collagen. Collagen content within the slurry was adjusted to approximately 10 mg/ml using a hydroxyproline assay and additional 0.01N HCl to adjust the content as needed. Before combining with the platelet component of the hydrogel, the collagen slurry was mixed with 30% 0.1M HEPES, 20% 10× Ham's F10, 30% Penicillin/streptomycin/amphoptericin B and 30% sterile water. The collagen slurry was then neutralized to a pH of 7.4 using 7.5% sodium bicarbonate.

PRP Preparation:

Whole blood was drawn from the jugular vein of each pig into tubes containing sodium citrate immediately prior to surgery. The blood was centrifuged to isolate the platelet-rich plasma (PRP) fraction at 100 g for 14 minutes. This resulted in an approximately 2× enrichment of the platelet concentration of the blood from a range of 495 to 567 K/mm$^3$ to 780 to 2300 K/mm$^3$. To make the platelet poor plasma (PPP), the anticoagulated blood was centrifuged at 200 g for twenty minutes, resulting in platelet counts of 18 K/mm$^3$ and 14 K/mm$^3$ in the two samples. The PRP or PPP was added to the collagen slurry to keep the plasma-collagen ratio at 1:1. The mixture was kept on ice until use.

Surgical Procedure:

IACUC approvals were obtained for this study prior to any surgical procedures. The pigs were pre-medicated with telazol 4.4-6.6 mg/kg intra-muscular (IM), xylazine 1.1-2.2 mg/kg IM, and atropine 0.04 mg/kg. They were intubated and placed on isoflurane 1-3% for anesthesia maintenance. After anesthesia had been obtained, the pigs were weighed and range of motion of each knee measured using a goniometer. The pigs were then placed in the supine position on the operating room table. Both hind limbs were shaved, prepared with chlorhexidine followed by betadyne paint and sterilely draped. To expose the ACL, a four-centimeter incision was made over the medial border of the patellar tendon. The incision was carried down sharply through the synovium. All sharp dissection after the skin incision was done using electrocautery for hemostasis. The fat pad was released from its proximal attachment and partially resected to expose the intermeniscal ligament. The intermeniscal ligament was released to expose the tibial insertion of the ACL. A Lachman maneuver was performed prior to releasing the ACL to verify knee stability. Two #1 Vicryl sutures were secured in the distal ACL stump using a modified Kessler stitch and the ends clamped. The ACL was transected completely using a No. 12 blade. Complete transection was verified visually and with a repeat Lachman maneuver. An absorbable suture anchor (TwinFix AB 5.0 Suture Anchor with DuraBraid Suture (USP #2); Smith & Nephew, Inc, Andover Mass.) was placed at the back of the femoral notch. The knee was irrigated with 500 cc of sterile normal saline to remove all synovial fluid. Hemostasis was carefully achieved using pressure and a solution of 1:10,000 of epinephrine as needed. Once hemostasis had been achieved, a strip of Gelfoam was presoaked in one batch of the collagen-PRP mixture and threaded onto sutures and up into the region of the proximal ACL stump in the notch. The sutures were tied with the knees in resting flexion (approximately 70 degrees) and a second batch of the collagen-platelet mixture was placed on top of the Gelfoam in the experimental knees. The knee was closed after the gel reached a soft set (approximately 10 minutes). The knee was left in resting extension while the suture repair alone was performed on the contralateral knee (approximately 1 hour). The procedure was identical in the suture repair alone knees, with the exception of the placement of the Gelfoam sponge and collagen-PRP hydrogel. In the collagen-PPP group, the procedure was identical to the PRP group, with the substitution of the platelet poor plasma for the platelet rich plasma in the collagen-platelet hydrogel. The incisions were closed in layers.

The animals were not restrained post-operatively and were allowed ad lib activity. Once the animals recovered from anesthesia, they were permitted to resume normal cage activity and nutrition ad lib. Banamine 1.1 mg/kg IM once and a Fentanyl patch 1-4 ug/kg transdermal were provided for post-operative analgesia. All animals were weight bearing on their hind limbs by 24 hours after surgery. After four weeks in vivo, the animals were again anesthetized and underwent in vivo MR imaging using the protocol detailed below.

After the magnetic resonance images had been obtained, the animals were euthanized using Fatal Plus at 1 cc/10 lbs. There were no animals which had any surgical complications or difficulty walking normally, redness, warmth and swelling of the knee, fever or other signs of infection that would have necessitated early euthanasia. The knees were retrieved and taken for immediate ex vivo MR imaging and same-day biomechanical testing. The knees were kept at 4° C. until biomechanical testing and kept moist using a saline spray and moist wraps.

Magnetic Resonance Imaging

In vivo magnetic resonance imaging was performed at 1.5 Tesla (GE Medical Systems, Milwaukee, Wis.) with a dedicated surface coil at the specified time points. Scanning was performed with the knees held in 30 degrees of flexion. Conventional MR images included T1 and 3D FSE proton density sequences. Multisection-multiechoT2 sequence for mapping T2 relaxation time were obtained with the following imaging parameters: TR/TE, 4000/14-98 in 14-msec increments for a total of 7 echo images with a 3-mm slice thickness. Perfusion was evaluated by using spoiled gradient echo sequence (TR/TE=200/2 ms, flip angle=60, 3 mm slice thickness, and 0.625 mm in plane resolution) with an intravenous contrast agent (Magnevist; Berlex, Wayne, N.J.) injected 10 s after the start of scan. Five images were obtained per slice, 78 s apart. Post contrast T1-weighted images were obtained (TR/TE=500/9 ms) in the coronal and sagittal planes with a 3-mm slice thickness.

Ex vivo magnetic resonance imaging was conducted on a 4.7 Tesla microimaging system (Biospec™, Bruker BioSpin MRI, Inc., Karlsruhe, Germany). The system consisted of three-axis self-shielded magnetic field gradients, with 30 G/cm maximum gradient amplitude in all three channels. The six-week treated, and intact knee specimens were placed in the radiofrequency coil (I.D. 72 mm) with the knee flexed 30 degrees as verified by goniometer. After the T2 localizers imaging on three orthogonal axes, spin-echo proton density weighted images (PD-WIs) were subsequently acquired in the sagittal and axial planes at the ACL site. The pulse sequence used was a conventional spin-echo sequence with following parameters: repetition time (TR)=2 sec, echo time (TE)=10 msec, band width=100 kHz, field of view=50 mm, matrix size=256×256, slice thickness=1 mm (gapless), number of slices=15, affording a total scan time of approximately 8.5 minutes.

Biomechanical Testing

The bone-ligament-bone ACL complex from both knees for each pig was tested in uniaxial tension. After euthanasia, the hind limb of each pig was amputated through the midshaft of the femur and tibia and the skin and overlying muscle removed. The joint capsule, MCL, lateral collateral ligament and the posterior cruciate ligament were kept intact during the embedding process and preserved until just prior to mechanical testing to facilitate correct spacing and alignment of the femur and tibia during mounting of the knee in the mechanical test apparatus. The ACL was maintained in a hydrated state throughout preparation and mechanical testing by wrapping the dissected knee in gauze and irrigating repeatedly with 0.9% saline. Temperature was maintained at room temperature to allow comparison with other published studies. The femur and tibia were cut to four inches in length and the ends embedded in cylindrical molds using polymethylmethacrylate (PMMA) resin. One or two transversely oriented, self-tapping drywall screws were placed unicortically in the proximal femur and distal tibia prior to embedding to prevent inadvertent pullout of the femur and/or tibia from the PMMA during mechanical testing. A specially designed jig was used to position the femur and tibia in the cylindrical molds with the knee flexed to 30° to align the femoral and tibial attachments of the ACL coaxial with the line of action of the load actuator. A goniometer was used to measure the overall alignment and orientation of the femur, tibia and ACL complex before embedding. After approximately 30 minutes cure time, the specimens are positioned in the grips and the remaining soft tissue attachments sectioned so that only the ACL was capable of resisting distraction across the knee joint during mechanical tensile testing.

All mechanical testing was conducted using an Interlaken Series 3300 Load frame (Eden Prairie, Minn.) controlled by an MTS TestStar IIm Digital Controller (Eden Prairie, Minn.). All test parameters were preprogrammed, and all phases of testing were executed automatically so as to maintain consistency during testing of all the specimens. Once the specimen was locked in the grips, the force and displacement transducers were zeroed. Close-range digital images of the bone-ligament-bone ACL complex were acquired at 3 Hz using a high resolution digital camera with a macro lens (PixeLINK PLA662 Megapixel Firewire camera, PixeLINK, Ottawa ON, Canada) so that the portion of the ACL that failed (i.e. midsubstance at repair site, femoral or tibial attachment sites) could be observed directly. Before conducting the tensile test, the bone-ligament-bone ACL complex was preconditioned with ten cycles of loading and unloading at a strain amplitude of approximately 3%, at a rate of 5 mm/min (Sakai, T.; Yasuda, K.; Tohyama, H.; Azuma, H.; Nagumo, A.; Majima, T.; and Frank, C. B.: Effects of combined administration of transforming growth factor-betal and epidermal growth factor on properties of the in situ frozen anterior cruciate ligament in rabbits. *Journal of Orthopaedic Research,* 20(6): 1345-51, 2002) to eliminate any "slack" in the test setup and to minimize viscoelastic effects (creep and stress-relaxation). Immediately after preconditioning, each specimen was tested to failure in uniaxial tension at 20 mm/min (Sakai, T.; Yasuda, K.; Tohyama, H.; Azuma, H.; Nagumo, A.; Majima, T.; and Frank, C. B.: Effects of combined administration of transforming growth factor-betal and epidermal growth factor on properties of the in situ frozen anterior cruciate ligament in rabbits. *Journal of Orthopaedic Research,* 20(6): 1345-51, 2002; Katsuragi, R.; Yasuda, K.; Tsujino, J.; Keira, M.; and Kaneda, K.: The effect of nonphysiologically high initial tension on the mechanical properties of in situ frozen anterior cruciate ligament in a canine model. *American Journal of Sports Medicine,* 28(1): 47-56, 2000). The applied actuator displacement and resultant force data were acquired at 10 Hz. After mechanical testing was completed, the proximal and distal portions of the ruptured ACL were explanted from the bone and submitted for further gross and microscopic analysis.

The tangent modulus (maximum slope of force-displacement curve), maximum load at failure and total work to failure (area under force-displacement curve) were determined from the force-displacement curve measured for each bone-ligament-bone ACL complex tested. Data was analyzed using MATLAB (The Math Works, Natick, Mass.). The yield load represents the point along the normalized force-displacement curve where the mechanical behavior of the ACL complex departed from "linear" behavior and for the purposes of this analysis was defined as the point where the tangent modulus declines by at least 2% from its maximum value. The ultimate load was deduced from the maximal normalized load sustained by the ACL complex prior to failure. The work to failure was derived by integrating the total area under the force-displacement curve.

Magnetic Resonance Imaging

In vivo MRI demonstrated a large mass of scar tissue in the area of the ACL transections treated with suture and collagen-platelet hydrogel, with a smaller mass seen in the region of the ACL when sutures alone were used (FIG. 4). In the knees treated with suture and the collagen-platelet hydrogel, the tissue in the region of the ACL appeared to be developing linear densities consistent with collagen fascicles within the mass, coursing from femur to tibia. The fat pad anterior to the scar mass in the knees treated with suture and collagen-platelet hydrogel also enhanced strongly immediately on perfusion of the knee with the IV gadolinium contrast, whereas the knee treated with suture repair alone had less visible enhancement (FIG. 5). The difference in scar size and perfusion between the knees treated with suture alone and the knees treated with suture and collagen-platelet hydrogel was seen on the post-gadolinium coronal images as well (FIG. 6).

Biomechanics

Failure Mode: In the ligaments treated with absorbable suture repair alone or suture repair augmented with platelet poor hydrogel, the mode of failure was intra-substance in 6 out of 6 ligaments, while in those treated with suture repair+PRP-hydrogel, the repaired ligaments failed at the bone-ligament junction in 2 out of 5 cases (FIG. 7; Table 1). In the intact ligaments, failure was at the bone-ligament junction in 6 out of 6 cases. The absorbable suture material used in the suture repairs appeared to be completely resorbed at the four-week time point.

Load at Yield: After four weeks in vivo, the suture repairs augmented with collagen-PRP hydrogel had a load at yield almost three times as high as the repairs performed with suture repair alone (Table 1). The yield load of the collagen-PRP group reached 65% of the yield load of the intact ACLs (179+/−37N) during these four weeks in vivo. The strength of the suture repair+PRP-hydrogel was significantly greater than that of the suture repairs alone, but both groups were still significantly lower than the intact ACL at four weeks (ANOVA, $p<0.0001$ for group, Bonferroni-Dunn correction post-hoc testing $p<0.008$ for all comparisons).

Maximum Load: After four weeks in vivo, the suture repairs augmented with collagen-PRP hydrogel held a maximum load that was twice as high as the repairs performed with suture repair alone (Table 1). The maximum load of the collagen-PRP group reached 57% of the maximum load of the intact ACLs (179+/−37N) during these four weeks in vivo. The strength of the suture repair+PRP-hydrogel was significantly greater than that of the suture repairs alone, but both groups were still significantly lower than the intact ACL at four weeks (ANOVA, $p<0.0001$ for group, Bonferroni-Dunn correction post-hoc testing $p<0.008$ for all comparisons).

Displacement at Yield: While the mean value of displacement at yield was lower in the repairs augmented with collagen-PRP hydrogel than in the suture repairs alone (Table 1), differences between the four groups were not found to be significant (ANOVA, $p>0.07$ for group, $p>0.008$ for all comparisons).

Stiffness: After four weeks in vivo, the stiffness of the suture repairs augmented with collagen-PRP hydrogel was twice as high as the repairs performed with suture repair alone (Table 1). The stiffness of the collagen-PRP group reached 50% of the stiffness of the intact ACLs during these four weeks in vivo. The stiffness of the suture repair+PRP-hydrogel was significantly greater than that of the suture repairs alone, but both groups were still significantly lower than the intact ACL at four weeks (ANOVA, $p<0.0001$ for group, Bonferroni-Dunn correction post-hoc testing $p<0.008$ for all comparisons).

Energy to Failure: The energy to failure in the suture repair+PRP-hydrogel groups was not statistically different from that in the group treated with suture repair alone using the multiple group comparison model (ANOVA, Bonferroni Dunn post hoc testing $p>0.04$). The difference between the suture repair+PRP-hydrogel group and the intact ligaments was also not significant ($p>0.08$). In contrast, the ligaments treated with suture repair alone had a significantly lower energy to failure than the intact ligaments ($p<0.001$).

The effect of platelet depletion on biomechanical parameters: When platelet poor plasma was used in the collagen-platelet hydrogel, there was no significant difference found between the collagen-PPP groups and the suture repairs alone. This was true for all biomechanical parameters including the load at yield ($p>0.50$), maximum load ($p>0.45$), displacement at yield ($p>0.70$), stiffness ($p>0.25$) and energy to failure ($p>0.39$). The collagen-PPP group had significantly lower yield load, maximum load and stiffness when compared with the collagen-PRP group ($p<0.006$ for all comparisons).

TABLE 1

Biomechanical Properties of the ACL Four Weeks after Transection and Repair

| Group | Surgery/Retr completed | Failure At B-L jn | Load@Yield (N) | Maximum Load (N) | Stiffness (N/mm) | Displ@Yield (mm) | Energy to Fail (N * mm) |
|---|---|---|---|---|---|---|---|
| Intact ACL | n = 6 | 100% | 142 +/− 38 | 179 +/− 37 | 48.6 +/− 7.9 | 4.7 +/− 0.7 | 492 +/− 204 |
| Suture Alone | n = 7 | 0% | 33 +/− 18 | 42 +/− 24 | 9.8 +/− 8.7 | 9.4 +/− 3.7 | 161 +/− 83 |
| Suture + PPP | n = 2 | 0% | 19 +/− 4 | 25 +/− 9 | 4.4 +/− 2.2 | 10.7 +/− 0.8 | 145 +/− 112 |
| Suture + PRP | n = 5 | 40% | 93 +/− 10 | 103 +/− 12 | 24.2 +/− 4.9 | 6.1 +/− 1.3 | 337 +/− 122 |

All values represent the mean +/− the standard deviation of the mean.

This study demonstrates that the biomechanical outcomes of strength and stiffness after primary repair of the ACL can be enhanced with use of a collagen-platelet rich hydrogel placed as a substitute provisional scaffold in the ligament defect. This is a critical finding as prior research into stimulation of healing in articular tissue defects has focused on overcoming cellular deficiencies rather than scaffolding deficiencies. In this study, no cells (except the platelets and white blood cells contained in the platelet-rich plasma) were transplanted, yet a highly cellular repair tissue was seen within the defect after only four weeks. This suggests that at least in the ACL, there is a sufficient intrinsic and/or extrinsic cellular response from the environment around the transected ACL to stimulate histologic healing of the defect if an appropriate scaffold is provided.

The advantages of this large animal model of complete ACL transection and suture repair are multiple. The suture repair provides initial mechanical stability, and the use of absorbable suture that has minimal strength at the end points of interest prevents the need for searching through (and possibly destroying) the scar mass to release suture and allow for testing of the scar mass itself. Use of a large animal model allows for easy identification of the structures of interest, both at the time of ligament transection and retrieval, and ease of mechanical repair for surgeons versed in repair of human ligaments. Additional testing looking at the results of a complete ACL transection left unrepaired for a period of time before surgical treatment would be beneficial, as most patients will not be able to undergo immediate repair; however, the costs of multiple animal surgeries and the additional housing were beyond the funds available for this project.

The collagen-platelet rich hydrogel used here also has several major advantages over prior tissue engineered implants. There is no required cell or tissue harvest prior to implantation (other than phlebotomy). The collagen form used to mix with the platelet-rich plasma is similar to that used currently in plastic surgery procedures (Cooperman, L. S.; Mackinnon, V.; Bechler, G.; and Pharriss, B. B.: Injectable collagen: a six-year clinical investigation. *Aesthetic Plastic Surgery*, 9(2): 145-51, 1985; Patel, M. P.; Talmor, M.; and Nolan, W. B.: Botox and collagen for glabellar furrows: advantages of combination therapy. *Annals of Plastic Surgery*, 52(5): 442-7; discussion 447, 2004) where it is obtained either autologously or as a xenograft (Patel, M. P.; Talmor, M.; and Nolan, W. B.: Botox and collagen for glabellar furrows: advantages of combination therapy. *Annals of Plastic Surgery*, 52(5): 442-7; discussion 447, 2004; Sclafani, A. P.; Romo, T., 3rd; Parker, A.; McCormick, S. A.; Cocker, R.; and Jacono, A.: Autologous collagen dispersion (Autologen) as a dermal filler: clinical observations and histologic findings. *Archives of Facial Plastic Surgery*, 2(1): 48-52, 2000). Thus, future clinical application is likely to be relatively low risk, as opposed to treatment methods which require an additional procedure to procure cells for expansion (Adachi, N.; Sato, K.; Usas, A.; Fu, F. H.; Ochi, M.; Han, C. W.; Niyibizi, C.; and Huard, J.: Muscle derived, cell based ex vivo gene therapy for treatment of full thickness articular cartilage defects. *Journal of Rheumatology*, 29(9): 1920-30, 2002; Bellincampi, L. D.; Closkey, R. F.; Prasad, R.; Zawadsky, J. P.; and Dunn, M. G.: Viability of fibroblast-seeded ligament analogs after autogenous implantation. *J Orthop Res*, 16(4): 414-20, 1998), or stem cells, or implanted recombinant growth factors or even viral vectors for gene therapy (Adachi, N.; Sato, K.; Usas, A.; Fu, F. H.; Ochi, M.; Han, C. W.; Niyibizi, C.; and Huard, J.: Muscle derived, cell based ex vivo gene therapy for treatment of full thickness articular cartilage defects. *Journal of Rheumatology*, 29(9): 1920-30, 2002; Evans, C. H., and Robbins, P. D.: Genetically augmented tissue engineering of the musculoskeletal system. *Clin Orthop*, (367 Suppl): S410-8, 1999; Menetrey, J.; Kasemkijwattana, C.; Day, C. S.; Bosch, P.; Fu, F. H.; Moreland, M. S.; and Huard, J.: Direct-, fibroblast- and myoblast-mediated gene transfer to the anterior cruciate ligament. *Tissue Eng*, 5(5): 435-42, 1999).

The use of Gelfoam as a carrier for the collagen-platelet hydrogel may also have contributed to the strength of the enhanced repairs. While we did not run a control group with Gelfoam alone in this Example, the collagen-PPP repairs were performed using Gelfoam and had mechanical properties inferior to that of the collagen-PRP group, suggesting that the platelets in the PRP group are more critical in stimulating healing of the ACL transection than the carrier itself. In addition, while this is the first-time healing of a complete transection of the ACL has been demonstrated biomechanically, the recovery of biomechanical strength in the defect remained incomplete at four weeks.

Example 3

In this example, we demonstrate biomechanical healing using a sponge, with anchor and suture in the absence of additional repair material/PRP. We conclude that biomechanical healing of the porcine ACL after complete transection and immediate suture repair using a collagen sponge is a novel treatment for this injury that is significantly better than the current standard of care (ACL reconstruction).

Complete ACL transections were performed in five 30 kg Yorkshire pigs and repaired with a four stranded, absorbable suture repair using a suture anchor in the femur. In each animal, the repair was augmented with threading a collagen sponge onto the suture anchor before tying the sutures. No post-operative immobilization was used. The animals were survived for three months and then underwent in vivo magnetic resonance imaging followed by euthanasia and immediate biomechanical testing. Six control knees with intact ACLs from three additional animals were used as an intact ACL control group. The supplementation of suture anchor repair with a collagen sponge resulted in formation of a large scar mass in the region of the ACL. Load at yield, maximum load and ACL tangent modulus were all significantly higher in the suture anchor repairs augmented with collagen sponge than in ACL transections treated with the current standard of care (ACL reconstruction) at the same time point.

Experimental Design

Five 30 kg female skeletally immature 4-month-old Yorkshire pigs underwent ACL transection and suture anchor repair. All animals were treated on one side with suture anchor repair augmented with collagen sponge (n=5). All animals were euthanized after fourteen weeks. Just prior to euthanasia, the animals had in vivo MRI of both knees with gadolinium contrast to assess perfusion of the ACL wound site. Immediately after euthanasia, the knees were harvested biomechanical testing of the ACL complex performed as previously described. Intact ACLs (n=6) from a separate group of age-matched, gender-matched and weight-matched animals were used as a control group for the biomechanical studies.

Surgical Procedure:

Institutional Animal Care and Use Committee approvals were obtained for this study prior to any surgical procedures. The pigs were pre-medicated with telazol 4.4-6.6 mg/kg IM, xylazine 1.1-2.2 mg/kg IM, and atropine 0.04 mg/kg. They were intubated and placed on isoflurane 1-3% for anesthesia maintenance. After anesthesia had been obtained, the pigs were weighed and placed in the supine position on the operating room table. Both hind limbs were shaved, prepared with chlorhexidine followed by betadyne paint and sterilely draped. No tourniquet was used. To expose the ACL, a four-centimeter incision was made over the medial border of the patellar tendon. The incision was carried down sharply through the synovium using electrocautery. The fat pad was released from its proximal attachment and partially resected to expose the intermeniscal ligament. The intermeniscal ligament was released to expose the tibial insertion of the ACL. A Lachman maneuver was performed prior to releasing the ACL to verify knee stability. Two #1 Vicryl sutures were secured in the distal ACL stump using a modified Kessler stitch. The ACL was transected completely at the junction of the middle and proximal thirds using a No 12 blade. Complete transection was verified visually and with a repeat Lachman maneuver that became positive in all knees with no significant endpoint detected after complete transection. All knees were irrigated with sterile saline to remove synovial fluid before suture anchor placement. An absorbable suture anchor (TwinFix AB 5.0 Suture Anchor with DuraBraid Suture (USP #2); Smith and Nephew, Inc, Andover Mass.) was placed at the back of the femoral notch. The knee was irrigated with 500 cc of sterile normal saline to remove all synovial fluid. Hemostasis was carefully achieved using pressure and a solution of 1:10,000 of epinephrine as needed. Once hemostasis had been achieved, a collagen sponge was threaded onto sutures and up into the region of the proximal ACL stump in the notch. The sutures were tied with the knees in resting flexion (approximately 70 degrees of flexion). The additional collagen sponge filled the intercondylar notch. The incisions were closed in multiple layers with absorbable sutures.

The animals were not restrained post-operatively and were allowed ad lib activity. Once the animals recovered from anesthesia, they were permitted to resume normal cage activity and nutrition ad lib. Buprenex 0.01 mg/kg IM once and a Fentanyl patch 1-4 ug/kg transdermal were provided for post-operative analgesia. All animals were weight bearing on their hind limbs by 24 hours after surgery. After three months in vivo, the animals were again anesthetized and underwent in vivo MR imaging using the protocol detailed below.

After the magnetic resonance images had been obtained, the animals were euthanized using Fatal Plus at 1 cc/10 lbs. No animals had any surgical complications of difficulty walking normally, redness, warmth and swelling of the knee, fever or other signs of infection that would have necessitated early euthanasia. The knees were retrieved and taken for immediate ex vivo MR imaging and same-day biomechanical testing. The knees were kept at 4 degrees C. until biomechanical testing and kept moist using a saline spray and moist wraps.

The six intact control knees were obtained from age- gender- and weight-matched animals after euthanasia following surgical procedures to the chest. The hind limbs were frozen at −20 degrees C. for three months and thawed overnight at 4 degrees C. before mechanical testing. All other testing conditions for these knees were identical to those in the experimental groups.

Magnetic Resonance Imaging: In vivo magnetic resonance imaging was performed at 1.5 Tesla (GE Medical Systems, Milwaukee, Wis.) with an eight-channel phased array coil at the specified time points. Scanning was performed with the knees placed maximum extension (between 30 and 45 degrees of flexion). Conventional MR included multiplane T1, FSE PD and T2 weighted images. Field of view (FOV): 16-18 cm, matrix: 256×256, (repetition time/ echo time) TR/TE: 400/16, 2500/32, 3000/66 msec, echo train length (ETL): 8, bandwidth (BW): 15 kHz, slice thickness: 3, interslice gap: 1 mm). Perfusion was evaluated by using spoiled gradient echo sequence (TR/TE=200/2 ms, flip angle=60, 3 mm slice thickness, and 0.625 mm in plane resolution) with an intravenous contrast agent (Magnevist; Berlex, Wayne, N.J.) 0.2 ml/kg injected 10 s after the start of scan. Five images were obtained per slice, 78 s apart. Post contrast T1-weighted images were obtained (FOV:16 cm, matrix: 256×256, TR/TE: 400/9 msec, slice thickness: 3 mm, interslice gap: 1 mm) in the coronal and sagittal planes.

Biomechanical Testing: The bone-ligament-bone ACL complex from both knees for each pig was tested in uniaxial tension as previously described. In brief, testing was performed with the knee flexed at 30 degrees of flexion and at room temperature. Immediately after preconditioning, each specimen was tested to failure in uniaxial tension at 20 mm/min. Close-range digital images were acquired at 3 Hz using a high resolution digital camera with a macro lens (PixeLINK PLA662 Megapixel Firewire camera, PixeLINK, Ottawa ON, Canada) to determine failure mode. The yield load, displacement at yield, tangent modulus (maximum slope of force-displacement curve), maximum load at failure, displacement at failure and total work to failure (area under force-displacement curve) were determined from the force-displacement curve measured for each bone-ligament-bone ACL complex. The yield load represented the point along the normalized force-displacement curve where the mechanical behavior of the ACL complex departed from "linear" behavior and for the purposes of this analysis was defined as the point where the tangent modulus declines by at least 2% from its maximum value. The displacement at yield was the displacement recorded at this same point. The maximum load is the maximal normalized load sustained by the ACL complex prior to failure and the displacement at failure the displacement recorded at the maximum load. The energy to failure was derived by integrating the total area under the force-displacement curve.

Results

MAGNETIC RESONANCE IMAGING: In vivo MRI demonstrated a progressive maturation of the repaired ACL from the large, bulky scar mass seen at 4 weeks (Example 2) to an aligned structure with signal qualities indistinguishable from the normal ACL. The site of previous transection of the ACL was no longer visible. The healing ACLs appeared more organized into tighter fascicles at the three-month time point (FIG. 8). A synovial layer had been seen to form over the ligaments, and blood vessels were seen on the surface of the ligaments. FIG. 8: shows the gross appearance of the Intact ACL (8A) and repaired ACL (8B) at three months (arrows). Of note is the fascicular organization of the tissue on the left.

Mechanical Properties: The strength of the repairs using suture and collagen sponge averaged 52% of the intact ACL strength at the three-month time point. This is favorable in comparison with the strength of ACL reconstruction in animal models, where the strength at three and six months is only approximately 20% of the intact ACL (FIG. 9).

The stiffness of the suture anchor/collagen sponge repairs was 36% that of the intact ACL—this also compares favorably with the current standard of care (ACL Reconstruction) where the stiffness at 12 weeks is only 23% of the intact ACL (FIG. 9).

FIG. 9 shows biomechanical properties of Suture Anchor/ Sponge Repair vs the current standard of care for ACL injuries (ACL Reconstruction or ACLR, ACLR data from Hunt et al, 2005) at 3 months in vivo. All values are normalized by the properties of the intact ACL in the specific animal model to compensate for variation in animal size and anatomy. The strength of the primary repaired ligaments is more than three times as high as the ACL Reconstructed knees.

This Example demonstrates that the biomechanical outcomes of strength after primary repair of the ACL transection can be enhanced with the novel technique of a collagen sponge threaded on the suture anchor sutures and thus located within the repair site. The strength at three months after repair is over 50% of the normal ACL strength—a value more than twice as high as the strength of ACL reconstruction at similar time points. In summary, use of a collagen sponge can stimulate biomechanical healing after suture anchor repair. The data supports significant changes in our clinical approach to ACL rupture, from resection and replacement towards repair and regeneration. ACLR data from Hunt et al, 2005

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize or be able to ascertain using no more than routine experimentation, many equivalents to the specific embodiments of the invention described herein. Such equivalents are intended to be encompassed by the following claims.

All references disclosed herein are incorporated by reference in their entirety.

The invention claimed is:

1. A method of repairing a ruptured ligament, comprising:
   attaching a suture to a first bone;
   connecting the suture to a first ruptured end of a ligament or tendon, the first ruptured end of the ligament or tendon connected to a second bone; and
   positioning a scaffold along the suture between the first bone and the first ruptured end of the ligament or tendon.

2. The method of claim 1, further comprising:
   drilling a hole in a second bone; and
   connecting a second suture to the second bone with a second device.

3. The method of claim 1, wherein the first bone is one of a femur or a tibia and the second bone is the other of the femur or the tibia.

4. The method of claim 1, further comprising attaching a first device only indirectly to the scaffold.

5. The method of claim 1, further comprising treating the scaffold with a repair material.

6. The method of claim 5, wherein the repair material is a platelet or plasma.

* * * * *

UNITED STATES PATENT AND TRADEMARK OFFICE
CERTIFICATE OF CORRECTION

| | | |
|---|---|---|
| PATENT NO. | : 11,076,846 B2 | Page 1 of 1 |
| APPLICATION NO. | : 16/558824 | |
| DATED | : August 3, 2021 | |
| INVENTOR(S) | : Martha M. Murray | |

It is certified that error appears in the above-identified patent and that said Letters Patent is hereby corrected as shown below:

In the Specification

Column 1, Lines 20-21 should read:
Government Support
This invention was made with government support under Grant number AR049346, awarded by The National Institutes of Health. The government has certain rights in the invention.

Signed and Sealed this
Twenty-seventh Day of August, 2024

Katherine Kelly Vidal
*Director of the United States Patent and Trademark Office*